(12) United States Patent
Eldering et al.

(10) Patent No.: US 11,872,220 B2
(45) Date of Patent: Jan. 16, 2024

(54) METHODS AND COMPOSITIONS FOR TREATING B-CELL MALIGNANCIES

(71) Applicant: Janssen Pharmaceutica NV, Beerse (BE)

(72) Inventors: Eric Frederik Eldering, Amsterdam (NL); Karoline Kielbassa, Amsterdam (NL); Ulrike Philippar, Antwerp (BE); Andrew Steele, Doylestown, PA (US); Marco Vincent Haselager, Hilversum (NL); A. P. Kater, Amsterdam (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/882,695

(22) Filed: Aug. 8, 2022

(65) Prior Publication Data

US 2023/0074759 A1    Mar. 9, 2023

Related U.S. Application Data

(60) Provisional application No. 63/230,991, filed on Aug. 9, 2021.

(51) Int. Cl.
*A61K 31/4709* (2006.01)
*A61P 35/00* (2006.01)

(52) U.S. Cl.
CPC .......... *A61K 31/4709* (2013.01); *A61P 35/00* (2018.01)

(58) Field of Classification Search
CPC ............................ A61K 31/4709; A61K 35/00
USPC ........................................................ 514/312
See application file for complete search history.

(56) References Cited

U.S. PATENT DOCUMENTS

| | | | |
|---|---|---|---|
| 10,717,745 B2 | 7/2020 | Arora et al. | |
| 10,934,310 B2 | 3/2021 | Arora et al. | |

FOREIGN PATENT DOCUMENTS

| | | | | |
|---|---|---|---|---|
| WO | 2017100662 A1 | 6/2017 | | |
| WO | 2018119036 A1 | 6/2018 | | |
| WO | 2020169736 A1 | 8/2020 | | |
| WO | WO-2020169736 A1 | * | 8/2020 | ......... A61K 31/4725 |

OTHER PUBLICATIONS

Chonghaile, BH3 mimetics: Weapons of cancer cell destruction, Science Translation Medicine, vol. 11, Issue 475, DOI: 10.1126/scitranslmed.aaw5311, 2019 (Abstract).

Hallaert, et al., c-Abl kinase inhibitors overcome CD40-mediated drug resistance in CLL: implications for therapeutic targeting of chemoresistant niches, Blood, 112 (13), pp. 5141-5149, 2008.
International Search Report from PCT/EP2022/072257 dated Nov. 30, 2022, 13 pgs.
Merino et al., BH3-Mimetic Drugs: Blazing the Trail for New Cancer Medicines, Cancer Cell 34 (6), pp. 879-891, 2018.
Pan et al., Selective BCL-2 Inhibition by ABT-199 Causes On-Target Cell Death in Acute Myeloid Leukemia, Cancer Discovery, 4 (3), pp. 362-375, 2014.
Saba et al., MALT1 inhibition is efficacious in both naïve and ibrutinib-resistant chronic lymphocytic leukemia, Cancer Res. 77 (24), pp. 7038-7048, 2017, doi:10.1158/0008-5472.CAN-17-2485.
Schultze et al., CD40-Activated Human B Cells: An Alternative Source of Highly Efficient Antigen Presenting Cells to Generate Autologous Antigen-Specific T Cells for Adoptive Immunotherapy, J. Clin. Invest. 100 (11), pp. 2757-2765, 1997.
Urashima et al., CD40 Ligand Triggered Interleukin-6 Secretion in Multiple Myeloma, Blood, vol. 85, No. 7, pp. 1903-1912, 1995.

* cited by examiner

*Primary Examiner* — Yevgeny Valenrod

(57) ABSTRACT

The present disclosure relates to methods of treating a malignancy in a subject in need thereof. The method involves administering to the subject a combination therapy comprising: (i) an inhibitor of mucosa-associated lymphoid tissue lymphoma translocation protein 1 (MALT1) having the structure of Formula (I)

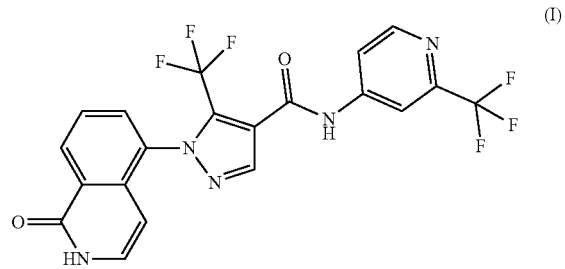

or a pharmaceutically acceptable salt, hydrate, polymorph, or solvates thereof, and (ii) an inhibitor of an anti-apoptotic Bcl-2 family protein, where the combination therapy is administered in an amount effective to treat the malignancy in the subject. Also disclosed are methods of reducing levels of regulatory T cells in a patient suffering from a malignancy, as well as combination therapeutics comprising an inhibitor of mucosa-associated lymphoid tissue lymphoma translocation protein (MALT1) having the structure of Formula (I) or a pharmaceutically acceptable salt, hydrate, polymorph, or solvates thereof, and an inhibitor of an anti-apoptotic Bcl-2 family protein.

32 Claims, 22 Drawing Sheets

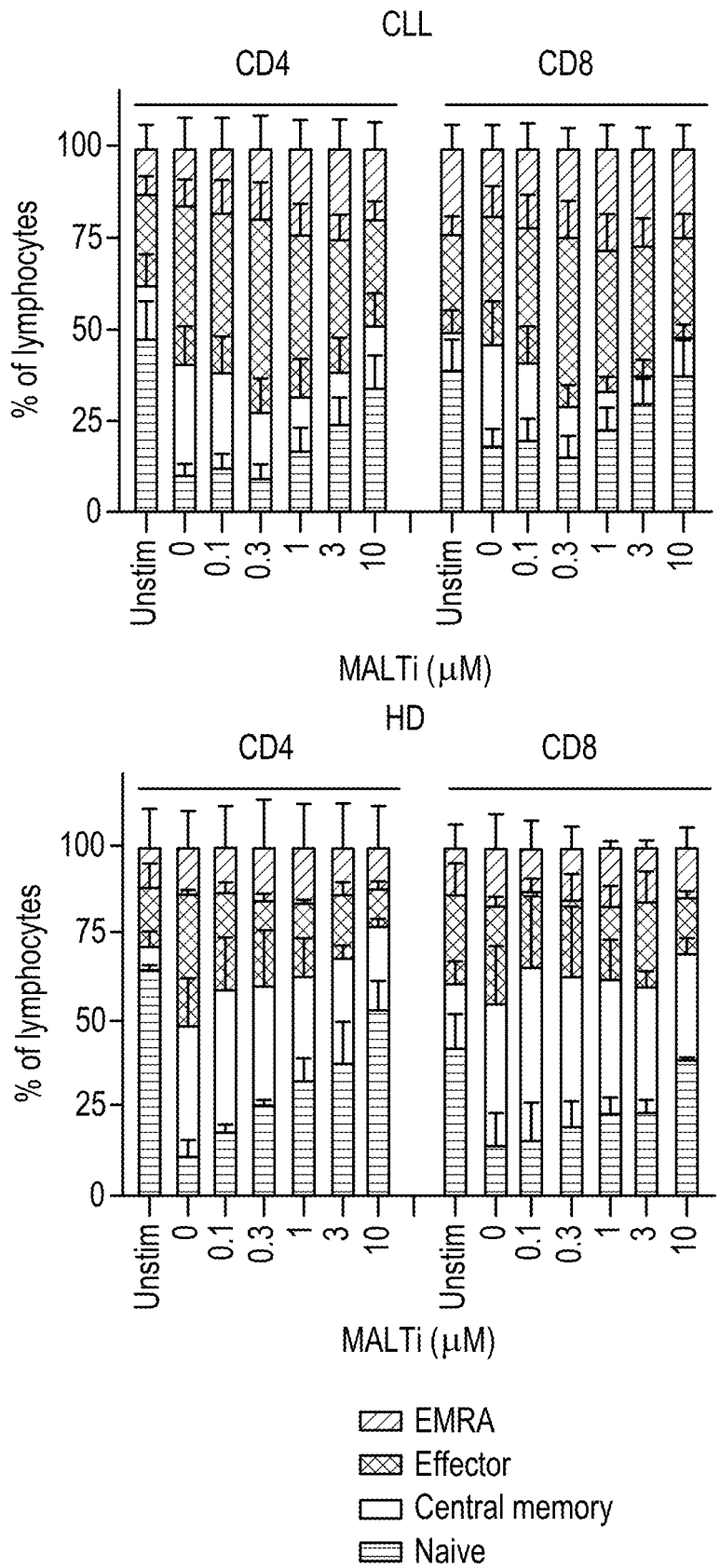

OCI-LY3 Tumor Growth curve (CARD11 mut)

- ■ Vehicle control
- ○ MALT1 inhibitor of Formula I, 30 mg/kg, BID
- ◇ MALT1 inhibitor of Formula I, 100 mg/kg, BID
- ⊖ Venetoclax, 40 mg/kg, BID
- ◆ MALT1 inhibitor of Formula I, 30 mg/kg, BID Venetoclax, 40 mg/kg, QD
- ● MALT1 inhibitor of Formula I, 100 mg/kg, BID Venetoclax, 40 mg/kg, QD

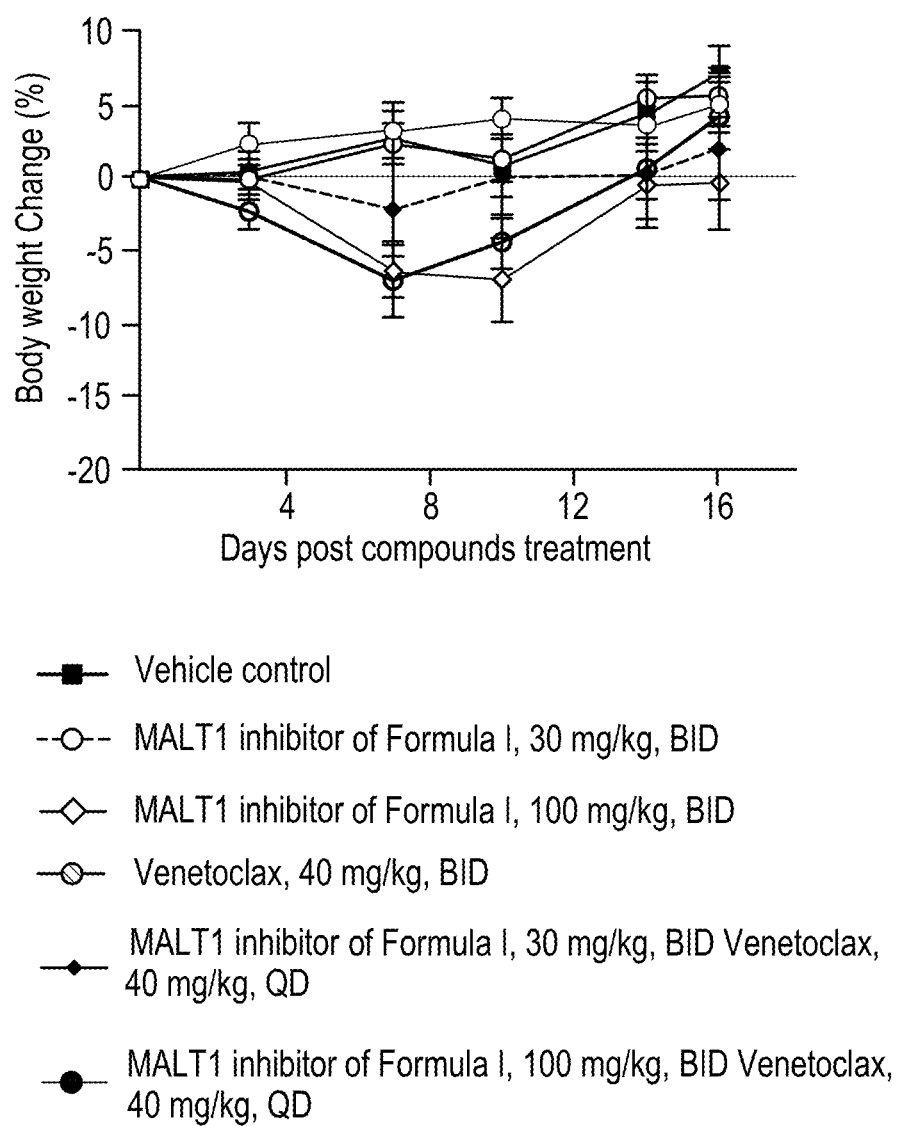

IL-10 in plasma OCI-LY3 Models
(16 days post treatment)

▭ Vehicle Group

▥ MALT1 inhibitor of Formula I, 30 mg/kg, BID

▨ MALT1 inhibitor of Formula I, 100 mg/kg, BID

▩ Venetoclax, 40 mg/kg, QD

▧ MALT1 inhibitor of Formula I, 30 mg/kg, BID Venetoclax, 40 mg/kg, QD

■ MALT1 inhibitor of Formula I, 100 mg/kg, BID Venetoclax, 40 mg/kg, QD

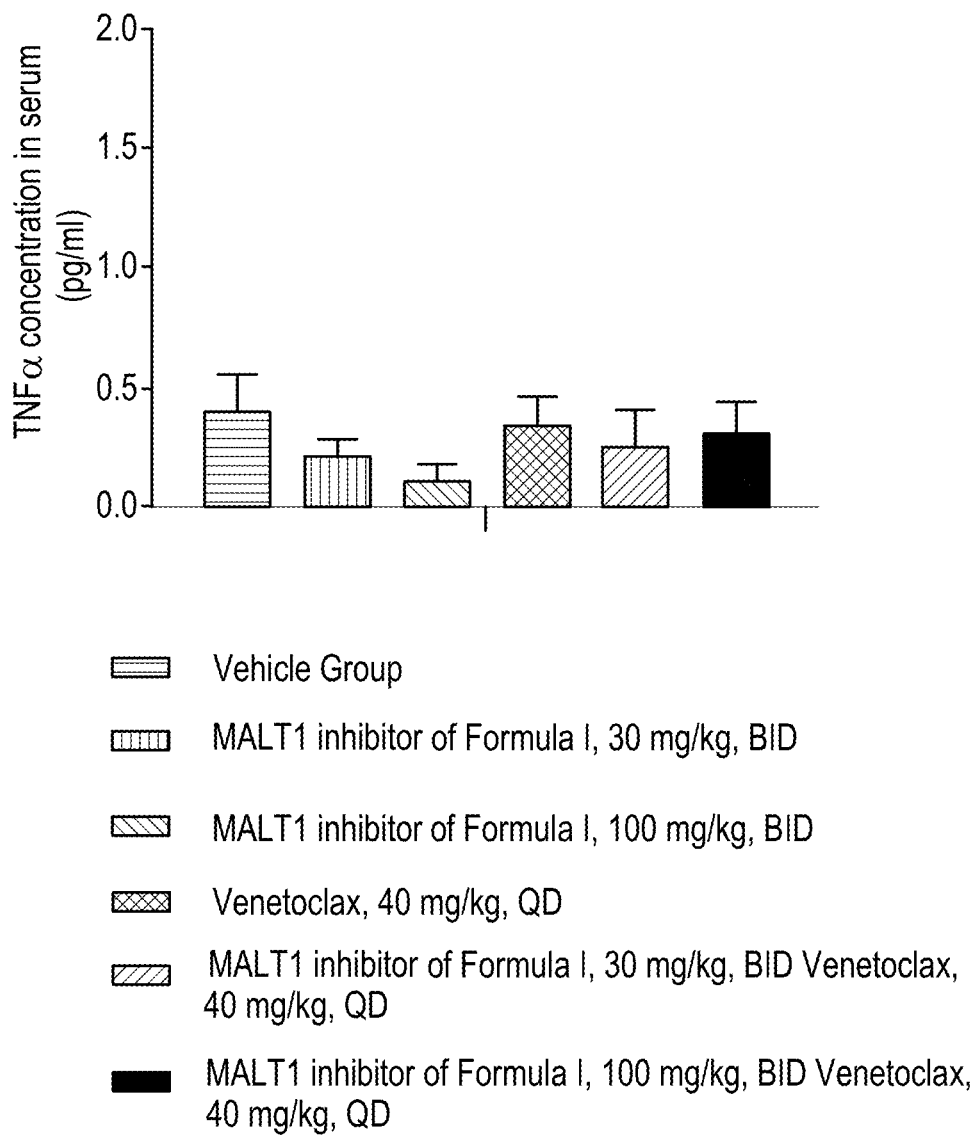

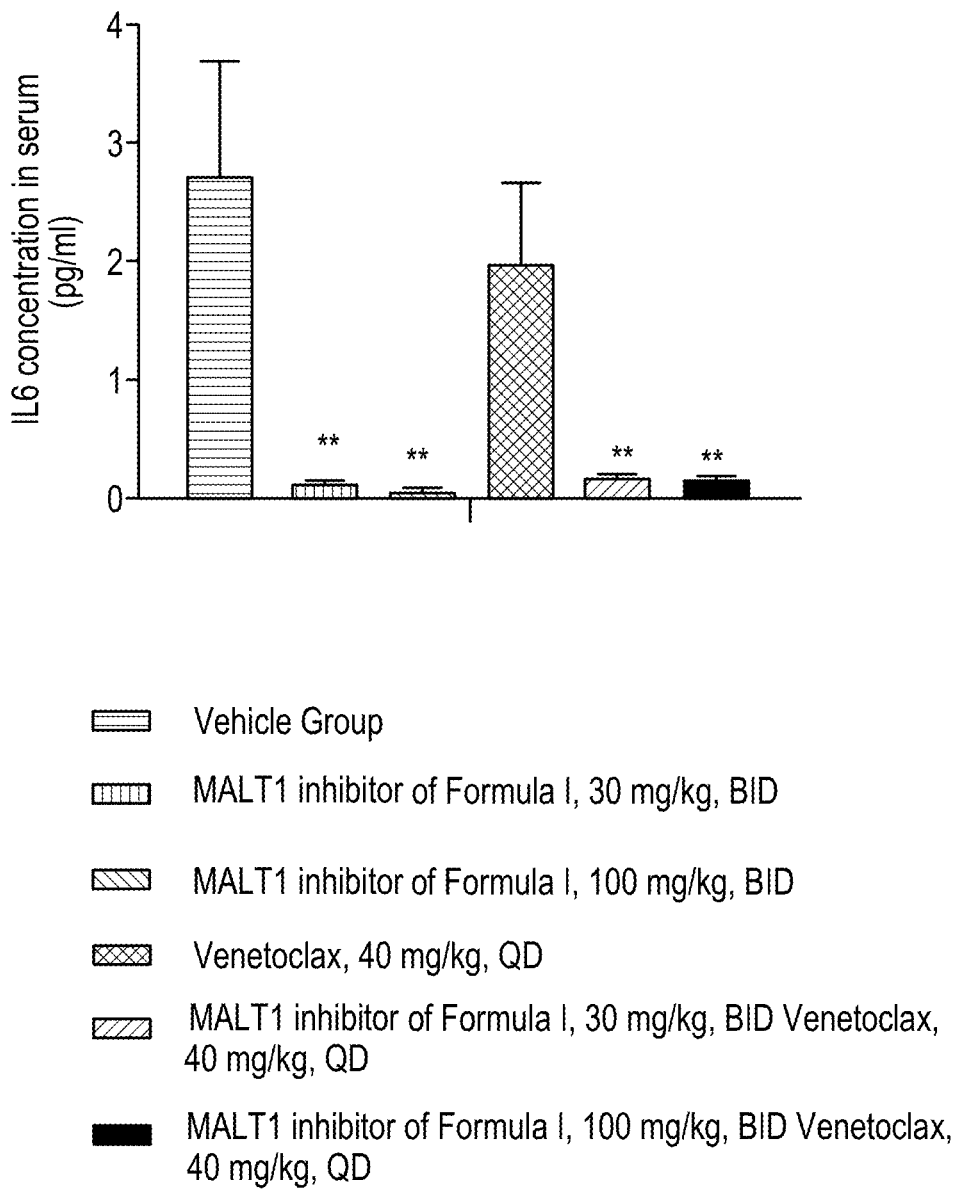

METHODS AND COMPOSITIONS FOR TREATING B-CELL MALIGNANCIES

CLAIM OF PRIORITY

This application claims priority to U.S. Provisional Application No. 63/230,991 filed on Aug. 9, 2021 titled "METHODS AND COMPOSITIONS FOR TREATING B-CELL MALIGNANCIES" which is incorporated herein by reference.

TECHNICAL FIELD

The present disclosure is directed to a combination therapy comprising an inhibitor of mucosa-associated lymphoid tissue lymphoma translocation protein and an inhibitor of an anti-apoptotic Bcl-2 family protein, and methods of use thereof.

BACKGROUND

Malignancies, in particular diffuse large B-cell lymphoma (DLBCL), mantle cell lymphoma (MCL), follicular lymphoma (FL), transformed follicular lymphoma (tFL), marginal zone lymphoma (MZL), chronic lymphocytic leukemia (CLL), small lymphocytic lymphoma (SLL), and Waldenström macroglobulinemia, continue to afflict patients. Alternative, effective treatments of cancer are still needed.

Chronic lymphocytic leukemia (CLL) is a B cell malignancy that strongly depends on microenvironmental stimuli for sustained growth and survival. This is underlined by the highly effective therapeutic targeting of the B cell receptor (BCR) signaling pathway by kinase inhibitors, which disrupt interactions between CLL cells and their growth-promoting lymph node (LN) microenvironment. The first two approved BCR pathway inhibitors are the Bruton tyrosine kinase (BTK) inhibitor ibrutinib and the phosphatidylinositol 3-kinase (PI3K) inhibitor idealisib. Both inhibitors have proven to be highly effective in the treatment of relapsed/refractory CLL in addition to ibrutinib as frontline therapy. Despite this success, drawbacks of these therapies have become apparent. Ibrutinib treatment can lead to adverse events such as atrial fibrillation and excessive bleeding, whereas idealisib treatment can cause serious immunological problems such as autoimmune colitis that limit its application. Moreover, despite high initial response rates, a significant proportion of patients acquire resistance to ibrutinib with progressive disease. Treatment options for this group of patients are very limited. Therefore, an urgent clinical rationale remains to develop additional strategies aimed at interrupting microenvironmental signals in CLL.

One potential target that may be therapeutically relevant is mucosa-associated lymphoid tissue lymphoma translocation protein 1 (hereinafter referred to as "MALT1"), which is a paracaspase that functions downstream of the BCR and TCR, including a spectrum of additional receptors involved in antigen binding. MALT1 plays a central role in NF-κB activation in response to antigen receptor signaling and since MALT1 is expected to function downstream of PI3K and BTK, it can be considered as a potential candidate target for CLL, especially in case of idelalisib and ibrutinib resistance or non-responsiveness. In CLL cells, engagement of the BCR leads to a cascade of tyrosine kinase phosphorylation resulting in the activation of BTK and PI3K, which phosphorylates downstream PLCγ2 and PKC. Activated PKC in turn then phosphorylates CARD 11, promoting the formation of the CBM complex consisting of CARD 11, BCL10 and MALT1. The scaffold function of the CBM complex leads to the recruitment of TRAF6 and TAK1 in order to activate the IKK complex, which in turn phosphorylates inhibitory IκB proteins and induce their proteolytic degradation. This leads to translocation of NF-κB proteins to the nucleus, where they can activate genes involved in proliferation, apoptosis inhibition, and inflammation. In addition, MALT1 contains proteolytic activity and may cleave negative regulators of NF-κB signaling, including RelB and A20, resulting in enhanced canonical NF-κB signaling.

Although MALT1 knockout mice display normal frequencies of B and T cells in immune organs, they have an absence of regulatory T cells, marginal zone B cells, and B1 B cells. Knockout of MALT1 does not affect upstream BCR or TCR signaling events, but does result into defective antigen receptor signaling upon antigen challenge as downstream signaling activity is blocked. Interestingly, knockin mice with a proteolytic inactive MALT1 mutant show signs of inflammatory autoimmune disease as a result of reduced regulatory T cells whereas lymphocyte responses are unaffected. Therefore, inhibition of MALT1 may result in both inhibition of CLL growth as well as enhanced anti-tumor immunity, thereby representing a promising therapeutic strategy in CLL. However, novel inhibitors and approaches to inhibiting this pathway are needed.

The present disclosure is directed to overcoming these and other deficiencies in the art.

SUMMARY

A first aspect of the present disclosure is directed to a method of treating a malignancy in a subject in need thereof. This method involves administering to the subject a combination therapy comprising: (i) an inhibitor of mucosa-associated lymphoid tissue lymphoma translocation protein 1 (referred to herein as "MALT1") having the structure of Formula (I)

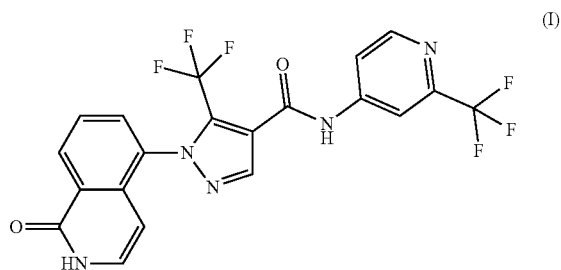

or a pharmaceutically acceptable salt, hydrate, polymorph, or solvates thereof, and (ii) an inhibitor of an anti-apoptotic Bcl-2 family protein. The combination therapy is administered in an amount effective to treat the malignancy in the subject.

A further aspect of the present disclosure relates to a method of reducing levels of regulatory T cells in a subject having a malignancy. This method involves administering, to said subject having the malignancy, a combination therapy comprising: (i) MALT1 having the structure of Formula (I) as shown herein above or a pharmaceutically acceptable salt, hydrate, polymorph, or solvates thereof, and (ii) an inhibitor of an anti-apoptotic Bcl-2 family protein. In accordance with this method, the combination therapy is administered in an amount effective to reduce regulatory T cell levels in the subject relative to the levels of regulatory T cells in the subject prior to said administering.

Another aspect of the present disclosure is directed to a combination therapeutic comprising: (i) MALT1 having the structure of Formula (I) as shown above, or a pharmaceutically acceptable salt, hydrate, polymorph, or solvates thereof, and (ii) an inhibitor of an anti-apoptotic Bcl-2 family protein.

As demonstrated in the Examples herein, monotherapy with a MALT1 inhibitor of the present disclosure in an animal model of B-cell lymphoma moderately inhibits in vivo growth, and treatment with the anti-apoptotic Bcl-2 family protein inhibitor shows little efficacy in this model. However, unexpectedly, the combination of these two therapeutic agents, i.e., MALT1 inhibitor and anti-apoptotic Bcl-2 family protein inhibitor, demonstrated a synergistic effect on tumor growth inhibition in this model. In addition, treatment with the MALT1 inhibitor alone or in combination the Bcl-2 family protein inhibitor downregulated IL-10, TNF-α, and IL12p70 secretion in serum of OCI-LY3 tumor bearing mice. Together this data supports the utility of this therapeutic combination for the treatment patients with B cell lymphomas.

BRIEF DESCRIPTION OF THE DRAWINGS

FIG. 1A is a bar graph showing the results of an experiment in which CLL cells were treated with the indicated drugs and concentrations and incubated for 24 hours. For the BCR stimulation, cells were supplemented with IL-4 and αIgM. Viability was measured using flow cytometry using DiOC6 and TO-PRO3 viability staining (n=9). Bars represent the mean±SEM. FIG. 1B is a bar graph showing the results of an experiment in which CLL cells were labeled with CellTrace Violet and cultured for 5 days on 3T40 supplemented with IL-21 or on 3T3 in combination with CpG, IL-2, IL-15, and IL-21 in combination with 10 μM MALTi. Proliferation was measured using flow cytometry based on CellTrace Violet signal (n=8). Results are shown as the mean±SEM, $*p<0.05$, $p<0.01$, $*p<0.001$ (paired sample t-test). FIGS. 1C-1E are bar graphs showing the results of experiments in which CLL cells were cultured on 3T40, stimulated with IL-4 and αIgM or stimulated with CpG, and incubated for 24 hours. Afterwards, culture supernatant was collected and IL-6 (n=14) (FIG. 1C), IL-10 (n=13) (FIG. 1D), and TNFα (n=14) (FIG. 1E) levels were measured using commercial ELISA kits. Bars represent the mean±SEM, samples were normalized to stimulated conditions without inhibitor, $*p<0.05$, $p<0.01$, $*p<0.001$, $****p<0.0001$ (paired sample t-test). FIGS. 1F-1H are images showing the results of experiments in which CLL cells were cultured on 3T40 (FIG. 1F), stimulated with IL-4 and αIgM (FIG. 1G) or stimulated with CpG (FIG. 1H) in combination with 10 μM MALTi, and incubated for 24 hours. Protein lysates were probed for p-IκBα, Bcl-XL, and actin as loading control.

FIGS. 2A-2C are bar graphs showing the results of experiments in which CLL cells were cultured for 24 hours on 3T40, stimulated with IL-4 and αIgM (soluble or immobilized to beads) or stimulated with CpG, and incubated for 24 hours in combination with 10 μM MALTi. Afterwards, expression of Bcl-XL (n=13) (FIG. 2A). Mcl-1 (n=8) (FIG. 2B) and Bcl-2 (n=9) (FIG. 2C) was measured using flow cytometry. Bars represent the mean±SEM, $***p<0.001$ (paired sample t-test). FIGS. 2D-2I) are graphs showing the results of experiments in which, in parallel, CD40-stimulated (n=9) (FIGS. 2D-2E), BCR-stimulated (n=8) (FIGS. 2F-2G), and TLR9-stimulated (n=6) (FIGS. 2H-2I) cells were with venetoclax or S63 for an additional 24 hours. Viability was measured using flow cytometry using DiOC6 and TO-PRO3 viability staining. Results are shown as the mean±SEM, $*p<0.05$, $p<0.001$, $*p<0.001$, $****p<0.0001$ (paired sample t-test).

FIGS. 3A-3E are bar graphs showing the results of experiments in which CLL (n=30) and healthy donor (n=8) PBMCs were labeled with CellTrace Violet, stimulated with anti-CD3 and anti-CD28 antibodies, and cultured for 4 days while simultaneously treated with indicated concentrations of MALTi. Afterwards, cells were measured using flow cytometry. FIG. 3A are bar graphs showing T cell activation measured based on CD25. FIG. 3B shows measurement of T cell activation in CLL (n=13) and healthy T cells (n=3) based on PD-1. FIG. 3C are bar graphs showing T cell proliferation measured based on CellTrace Violet signal. FIG. 3D are bar graphs showing T cell degranulation measured in CLL (n=13) and healthy (n=3) T cells based on CD107a. After incubation, culture supernatant was collected and IFNγ (n=12) and TNFα (n=9) levels were measured using commercial ELISA kits (FIG. 3E). Bars represent the mean SEM, $*p<0.05$, $p<0.001$, $*p<0.001$, $****p<0.0001$ (paired sample t-test).

FIGS. 4A-4C demonstrate that MALT1 inhibition specifically targets regulatory T cells. FIG. 4A shows result of an experiment where CLL (n=7) and healthy donor (n=2) PBMCs were stimulated with anti-CD3/CD28 antibodies and cultured for 4 days while simultaneously treated with indicated concentrations of MALTi. Afterwards, T cell subsets were measured using flow cytometry as described. FIG. 4B shows the results of an experiment in which unstimulated CLL (n=17) and healthy donor (n=5) PBMCs were cultured for 4 days while simultaneously treated with indicated concentrations of MALTi. Afterwards, T cell subsets were measured using flow cytometry based on CD27 and CD45RA. Naïve T cells were gated as CD27$^+$/CD45RA$^+$, central memory T cells were gated as CD27$^+$/CD45RA$^-$, memory T cells were gated as CD27$^-$/CD45RA$^-$, and terminally differentiated effector memory cells re-expressing CD45RA T cells were gated as CD27$^-$/CD45RA$^+$. FIG. 4C shows the results of an experiment in which unstimulated CLL (n=17) and healthy donor (n=5) PBMCs were cultured for 4 days while simultaneously treated with indicated concentrations of MALTi. Afterwards, regulatory T cells were measured using flow cytometry and gated as CD4$^+$/CD25$^+$/FoxP3$^+$. Bars represent the mean±SEM, $*p<0.05$, $***p<0.001$ (paired sample t-test).

FIGS. 6A-6F show tumor volume growth, mouse body weight change, and serum cytokine secretion levels in the OCI-LY3 mouse model after MALT1 Inhibitor of Formula I and Venetoclax combination treatment. FIG. 6A is a graph showing the OCI-LY3 tumor growth curve from day 0 to day 16 post treatment. FIG. 6B is a graph showing OCI-LY3 body weight from day 0 to day 16 post treatment. FIGS.

Figure 1A:
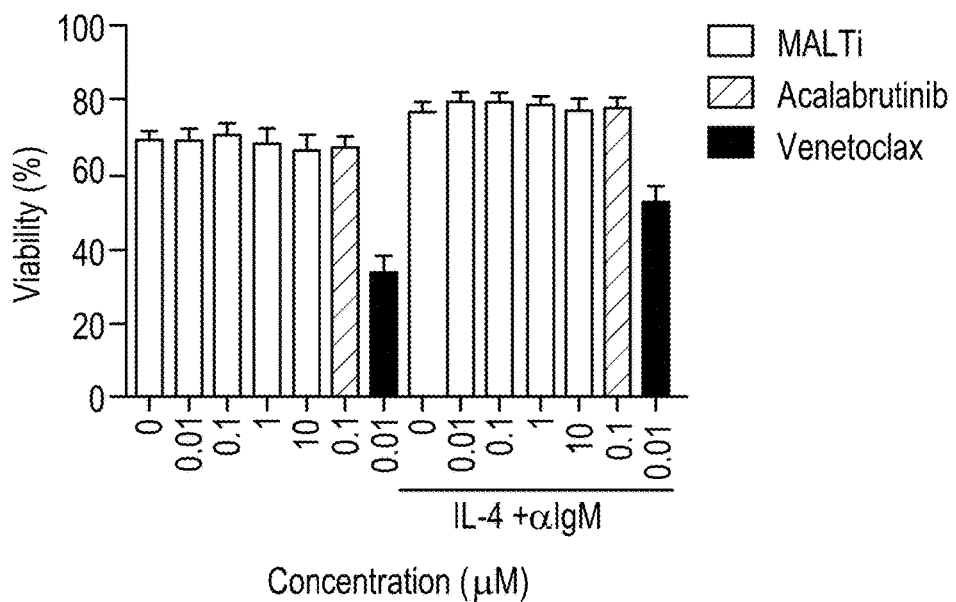
FIGS. 1A-1H demonstrate that MALT1 inhibition affects downstream NF-κB signaling in CLL cells including downstream of CD40.

6C-6F are graphs showing serum cytokine secretion levels of IL-10 (FIG. 6C), TNFα (FIG. 6D), IL12p70 (FIG. 6E), and IL6 (FIG. 6F) in plasma on day 16 post treatment, respectively.

DETAILED DESCRIPTION

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to aspects containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 component refers to groups having 1, 2, or 3 components. Similarly, a group having 1-5 cells refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed aspect.

The term "about" as used herein when immediately preceding a numerical value means a range of plus or minus 10% of that value, for example, "about 50" means 45 to 55, "about 25,000" means 22,500 to 27,500, etc., unless the context of the disclosure indicates otherwise, or is inconsistent with such an interpretation.

A first aspect of the present disclosure is directed to a method of treating a malignancy in a subject in need thereof. The method involves administering to the subject a combination therapy comprising: (i) an inhibitor of MALT1 having the structure of Formula (I)

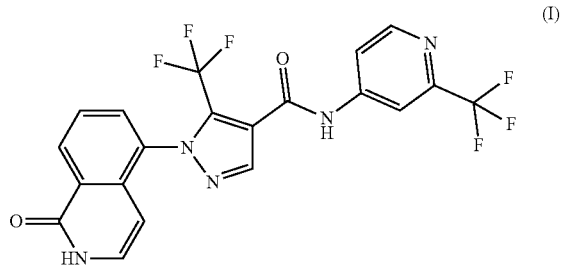

or a pharmaceutically acceptable salt, hydrate, polymorph, or solvates thereof, and (ii) an inhibitor of an anti-apoptotic Bcl-2 family protein, where the combination therapy is administered in an amount effective to treat the malignancy in the subject.

As used herein, "treating" or "treatment" of any disease, more specifically a malignancy refers, in some embodiments, to ameliorating the disease or malignancy (i.e., arresting or reducing the development of the disease or at least one of the clinical symptoms thereof). In other embodiments, "treating" or "treatment" refers to ameliorating at least one physical parameter, which may not be discernible by the subject. In further embodiments, "treating" or "treatment" refers to modulating the disease or malignancy, either physically, (e.g., stabilization of a discernible symptom), physiologically, (e.g., stabilization of a physical parameter), or both. In other embodiments, "treating" or "treatment" refers to delaying the onset of the disease or recurrence of the disease.

A further aspect of the present disclosure relates to a method of reducing levels of regulatory T cells in a subject having a malignancy. This method involves administering, to said subject having the malignancy, a combination therapy comprising: (i) an inhibitor of MALT1 having the structure of Formula (I)

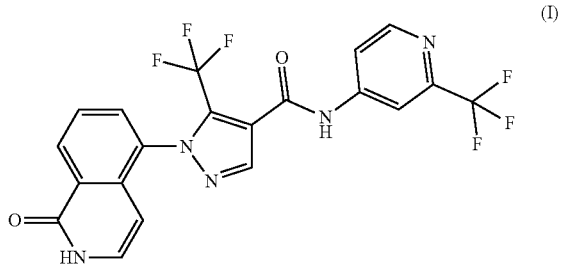

or a pharmaceutically acceptable salt, hydrate, polymorph, or solvates thereof, and (ii) an inhibitor of an anti-apoptotic Bcl-2 family protein, where the combination therapy is administered to the subject in an amount effective to reduce regulatory T cell levels in the subject relative to the levels of regulatory T cells in the subject prior to said administering.

As referred to herein, the terms "regulatory T cell" or "$T_{reg}$" refer to T cells that suppress an abnormal or excessive immune response and play a role in immune tolerance. Regulatory T cells are typically transcription factor Foxp3-positive $CD4^+$ T cells and can also include transcription factor Foxp3-negative regulatory T cells that are IL-10-producing $CD4^+$ T cells. In some embodiments of the methods disclosed herein, administration of the combination therapy achieves at least a 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more reduction in the amount of regulatory T cells in the subject relative to the levels of regulatory T cells in the subject prior to the administering step.

Subjects suitable for treatment in accordance with the methods disclosed herein have a malignancy. The malignancy may be a lymphoma, a leukemia, a carcinoma, a sarcoma, or any other known malignancy. As referred to herein, a "lymphoma" is a malignant neoplasm originating from lymphocytes; a "leukemia" is a class of hematological malignancies of bone marrow cells in which immortal clones of immature blood cells multiply at the expense of normal blood cells; a "carcinoma" is a malignant tumor that occurs in epithelial tissue and may infiltrate local tissues or produce metastases; and a "sarcoma" is a cancer arising from mesenchymal tissue such as muscle or bone, which may affect the bones, bladder, kidneys, liver, lungs, parotids, and spleen.

Lymphomas suitable for treatment in accordance with the methods disclosed herein include, without limitation, non-Hodgkin's lymphoma (NHL (including B-cell NHL)), diffuse large B-cell lymphoma (DLBCL), mantle cell lymphoma (MCL), follicular lymphoma (FL), transformed follicular lymphoma (tFL), mucosa-associated lymphoid tissue (MALT) lymphoma, marginal zone lymphoma (MZL), T-cell lymphoma, Hodgkin's lymphoma, small lymphocytic lymphoma (SLL), Waldenström macroglobulinemia, and Burkitt's lymphoma.

In some embodiments, the malignancy is a B-Cell lymphoma. B-cell lymphomas suitable for treatment in accordance with the methods disclosed herein include, without limitation, a diffuse large B-cell lymphoma (DLBCL), mantle cell lymphoma (MCL), follicular lymphoma (FL), transformed follicular lymphoma (tFL), marginal zone lymphoma (MZL), chronic lymphocytic leukemia (CLL), small lymphocytic lymphoma (SLL), Waldenström macroglobulinemia (WM), Burkitt's lymphoma, hairy cell leukemia, primary central nervous system lymphoma, and primary intraocular lymphoma.

In some embodiments, the malignancy is diffuse large B-cell lymphoma (DLBCL). DLBCL is an aggressive (fast-growing) NHL that affects B-lymphocytes and which can develop in the lymph nodes or in "extranodal sites" (areas outside the lymph nodes) such as the gastrointestinal tract, testes, thyroid, skin, breast, bone, brain, or essentially any organ of the body. In some embodiments, the diffuse large B-cell lymphoma (DLBCL) treated in accordance with the methods and compositions disclosed herein is activated B-cell (ABC)-DLBCL, germinal center B-cell (GCB)-DLBCL, or non-GCB-DLBCL.

In some embodiments, the malignancy to be treated is a leukemia. Leukemias suitable for treatment in accordance with the methods disclosed herein include, without limitation, chronic lymphocytic leukemia (CLL), lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia and multiple myeloma.

In any embodiment, the malignancy to be treated in accordance with the methods as disclosed herein may include, without limitation, brain (gliomas), glioblastomas, breast cancer, colorectal/colon cancer, prostate cancer, lung cancer, non-small-cell lung cancer, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, Chronic graft versus host disease, and gastrointestinal stromal tumor.

In any embodiment, the malignancy to be treated in accordance with the methods as disclosed herein may include, without limitation, non-Hodgkin's lymphoma (NHL (including B-cell NHL)), diffuse large B-cell lymphoma (DLBCL), mantle cell lymphoma (MCL), follicular lymphoma (FL), transformed follicular lymphoma (tFL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, primary and secondary central nervous system lymphoma, transformed follicular lymphoma, diseases/cancer caused by API2-MALT1 fusion, and GIST (gastrointestinal stromal tumor).

Suitable subjects to be treated in accordance with the methods and compositions disclosed herein include, without limitation, mammalian subject. Exemplary mammalian subjects include, without limitation, humans, non-human primates, dogs, cats, rodents (e.g., mouse, rat, guinea pig), horses, cattle and cows, sheep, and pigs. In some embodiments, the subject is a human subject. The terms "human," "patient," and "subject" are used interchangeably herein.

As described herein supra, the methods of the present disclosure involve the administration of a MALT1 inhibitor having the structure of Formula (I)

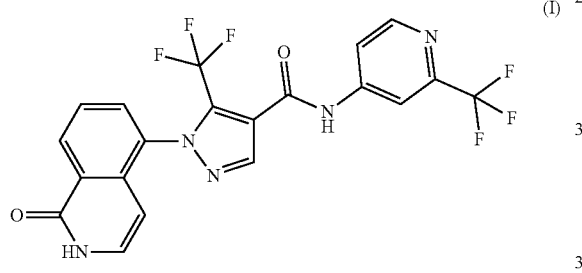

(I)

1-(1-oxo-1,2-dihydroisoquinolin-5-yl)-5-(trifluoromethyl)-N-[2-(trifluoromethyl)pyridin-4-yl]-1H-pyrazole-4-carboxamide, which is fully described in U.S. Pat. No. 10,954,214, which is hereby incorporated by reference in its entirety).

In any embodiment, a pharmaceutically acceptable salt, hydrate, polymorph, or solvate of the MALT1 inhibitor of Formula (I) is administered. The term "pharmaceutically acceptable" refers to a compound of the disclosure that has been approved or is approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The MALT1 inhibitor of Formula (I) may be prepared, for example, as described in Example 158 of WO 2018/119036 and WO 2020/169736, which are hereby incorporated by reference in their entirety.

In any embodiment of the methods disclosed herein, the MALT inhibitor may be a hydrate of a MALT1 inhibitor having the structure of Formula (I). As used herein, the term "hydrate" refers to a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A person of ordinary skill in the art appreciates that the MALT1 inhibitor of Formula (I) may exist as tautomers, and all tautomeric forms the MALT1 inhibitor of Formula (I) are encompassed by the disclosure and structure provided herein even if not specifically indicated. For example, it is understood that:

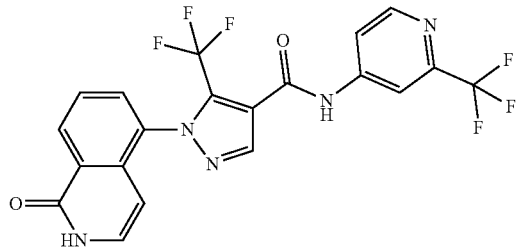

also encompasses by the following structure:

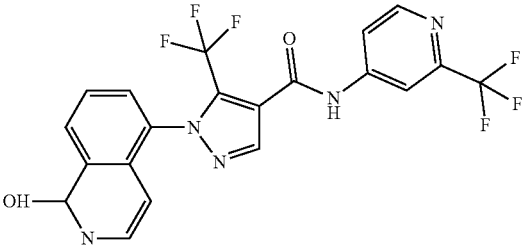

Any convenient tautomeric arrangement of the compound of Formula (I) are suitable for use in the compositions and methods described herein.

In any embodiment, the MALT1 inhibitor may be a pharmaceutically acceptable salt. A "pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

In any embodiment of the methods disclosed herein, the MALT1 inhibitor may be a polymorph of a MALT1 inhibitor having the structure of Formula (I). As used herein, the term "polymorph" refers to a specific form of a compound of the present disclosure, for example, polymorphs may represent crystalline forms that can vary in pharmaceutically relevant physical properties between one form to another, for example, under different crystallization conditions, environmental conditions, hygroscopic activity of the compounds, etc.

In any embodiment of the methods disclosed herein, the MALT1 inhibitor may be a solvate of a MALT1 inhibitor having the structure of Formula (I). As used herein, the term "solvate" refers to solvents combined with a compound of the present disclosure. Such solvents include, e.g., ethanol, acetone, ethylacetate, THF, acetonitrile, dichloromethane, 1,4-dioxane, acetic acid, toluene, water, n-heptane, toluene, n-pentane TBME, or any combination thereof.

The examples of the present disclosure demonstrate that administering a MALT1 inhibitor having the structure of Formula (I) as disclosed herein or a pharmaceutically acceptable salt, hydrate, polymorph, or solvate thereof and an inhibitor of an anti-apoptotic Bcl-2 family protein is effective to synergistically increase anti-tumor activity.

As described herein, the Bcl-2 family plays important roles in malignancies, including lymphomas, leukemias, carcinomas, and sarcomas.

In accordance with the methods disclosed herein, an inhibitor of an anti-apoptotic Bcl-2 family protein inhibitor is administered in combination with the MALT1 inhibitor. In any embodiment, the inhibitor is an inhibitor of apoptosis regulator Bcl-2 (gene name BCL2). In any embodiment, the inhibitor is an inhibitor of Bcl-2-like protein 1 (also known as Bcl2-L-1 and Apoptosis regulator Bcl-X) (gene names BCL2L1, BCLXL, BCL2L). In any embodiment, the inhibitor is an inhibitor of Bcl-L-2 (also known as Bcl-2-like protein and apoptosis regulator Bcl-W) (gene names BCL2L2 and BCLW). In any embodiment, the inhibitor is an inhibitor of Bcl2-L-3 (also known as induced myeloid leukemia cell differentiation protein Mcl-1, Bcl-2-like protein 3) (gene names MCL-1 and BCL2L3). In any embodiment, the inhibitor is an inhibitor of Bcl2-L-5 (also known as Bcl-2-related protein A1 and Bcl-2-like protein 5) (gene names BCL2A1, BCL2L5, BFL1, GRS, and HBPA1). In any embodiment, the inhibitor in an inhibitor of Bcl-L-10 (also known as Bcl-2-like protein 10) (gene names BCL2L10 and BCLB). In any embodiment, the inhibitor is pan-inhibitor, inhibiting any one or more of the aforementioned members of the Bcl-2 family of apoptotic proteins.

Suitable Bcl-2 family protein inhibitors for use in accordance with the methods disclosed herein include, without limitation, BH3 protein mimetic. BH3 protein mimetics are known in the art and described, for example, in Merino et al., "BH3-Mimetic Drugs: Blazing the Trail for New Cancer Medicines," *Cancer Cell* 34(6): 879-91 (2018) and Chonghaile, "BH3 Mimetics: Weapons of Cancer Cell Destruction," *Science Translational Medicine* 11(475):eaaw 5311 (2019).

Suitable Bcl-2 family protein inhibitors for use in accordance with the methods disclosed herein include, without limitation, those inhibitors provided in Table 1 below.

Table 1. Suitable Bcl-2 Family Protein Inhibitors

TABLE 1

Suitable Bcl-2 Family Protein Inhibitors

| Trade-name | Chemical Name | Structure |
| --- | --- | --- |
| ABT-199; venetoclax | 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) | 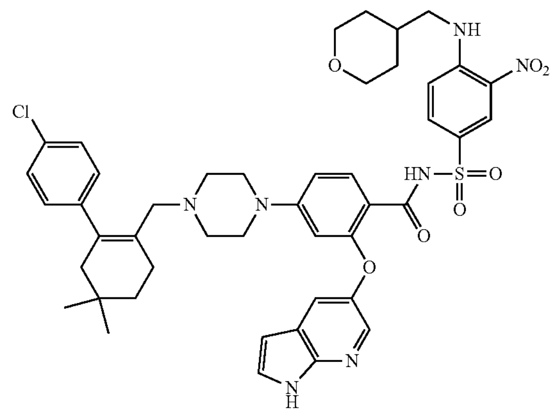 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |
| ABT-263; navitoclax | 4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide | 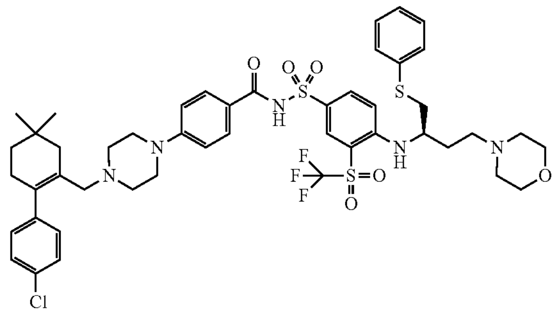 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |

TABLE 1-continued

Suitable Bcl-2 Family Protein Inhibitors

| Trade-name | Chemical Name | Structure |
| --- | --- | --- |
| ABT-737 | 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide | 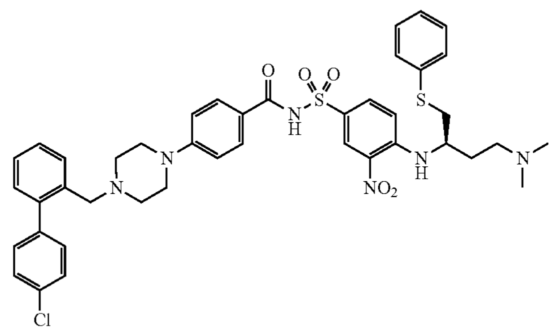 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| HA14-1 | ethyl 2-amino-6-bromo-4-(1-cyano-2-ethoxy-2-oxoethyl)-4H-chromene-3-carboxylate | 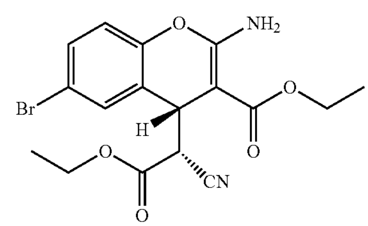 [SMILES: CCOC(=O)C1=C(N)Oc2ccc(Br)cc2[C@H]1[C@H](C#N)C(=O)OCC] |
| S55746; BCL201 | N-(4-hydroxyphenyl)-3-[6-[(3S)-3-(morpholin-4-ylmethyl)-3,4-dihydro-1H-isoquinoline-2-carbonyl]-1,3-benzodioxol-5-yl]-N-phenyl-5,6,7,8-tetrahydroindolizine-1-carboxamide | 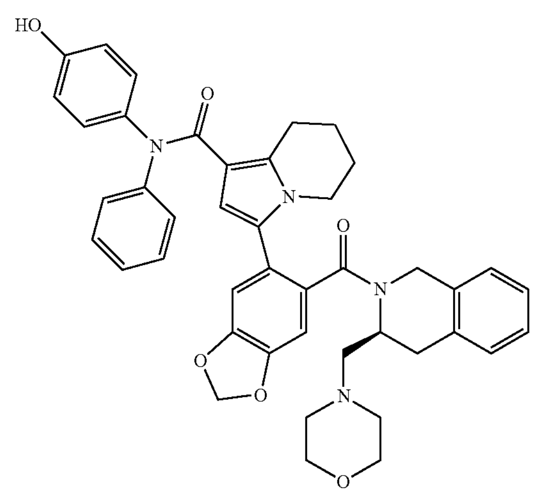 [SMILES: O=C(c1cc(-c2cc3c(cc2C(=O)N2Cc4ccccc4C[C@H]2CN2CCOCC2)OCO3)n2c1CCCC2)N(c1ccccc1)c1ccc(O)cc1] |
| BH3I-1 | 5-[(4-bromophenyl)methylene]-a-(1-methylethyl)-4-oxo-2-thioxo-3-thiazolidineacetic acid | 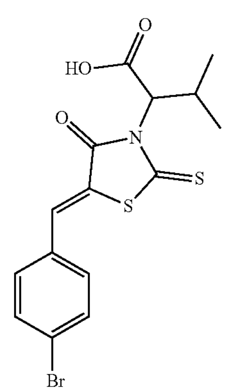 [SMILES: CC(C)C(C(=O)O)N1C(=O)/C(=C/c2ccc(Br)cc2)SC1=S] |

TABLE 1-continued

Suitable Bcl-2 Family Protein Inhibitors

| Trade-name | Chemical Name | Structure |
| --- | --- | --- |
| A-1155463 | 2-[8-(1,3-benzothiazol-2-ylcarbamoyl)-3,4-dihydro-1H-isoquinolin-2-yl]-5-[3-[4-[3-(dimethylamino)prop-1-ynyl]-2-fluorophenoxy]propyl]-1,3-thiazole-4-carboxylic acid | 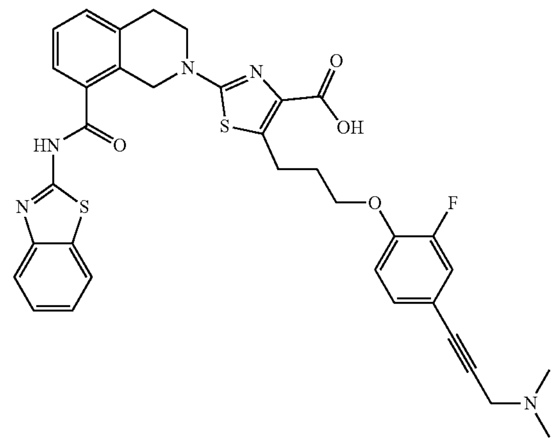 [SMILES: CN(C)CC#Cc1ccc(OCCCc2sc(N3CCc4cccc(C(=O)Nc5nc6ccccc6s5)c4C3)nc2C(=O)O)c(F)c1] |
| A-1331852 | 3-[1-(1-adamantylmethyl)-5-methylpyrazol-4-yl]-6-[8-(1,3-benzothiazol-2-ylcarbamoyl)-3,4-dihydro-1H-isoquinolin-2-yl]pyridine-2-carboxylic acid | 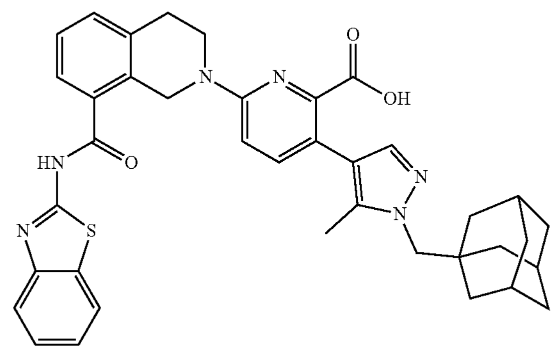 [SMILES: Cc1c(-c2ccc(N3CCc4cccc(C(=O)Nc5nc6ccccc6s5)c4C3)nc2C(=O)O)cnn1CC12CC3CC(CC(C3)C1)C2] |
| TW-37 | N-[4-(2-tert-butylphenyl)sulfonylphenyl]-2,3,4-trihydroxy-5-[(2-propan-2-ylphenyl)methyl]benzamide | 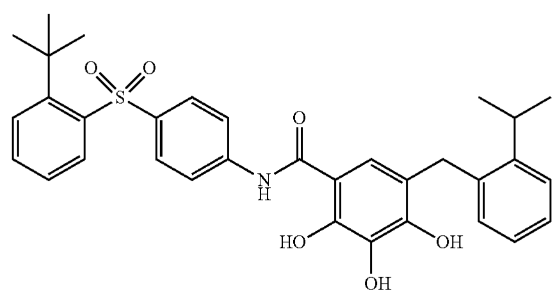 [SMILES: CC(C)c1ccccc1Cc1cc(C(=O)Nc2ccc(S(=O)(=O)c3ccccc3C(C)(C)C)cc2)c(O)c(O)c1O] |
| S44563 | (4aR)-3-[(4'-Chloro[1,1'-biphenyl]-2-yl)methyl]-N-[[4-[[(1R)-3-(dimethylamino)-1-[(phenylthio)methyl]propyl]amino]-3-nitrophenyl]sulfonyl]-2,3,4,4a,5,6-hexahydro-1H-pyrazino[1,2-a]quinoline-8-carboxamide | 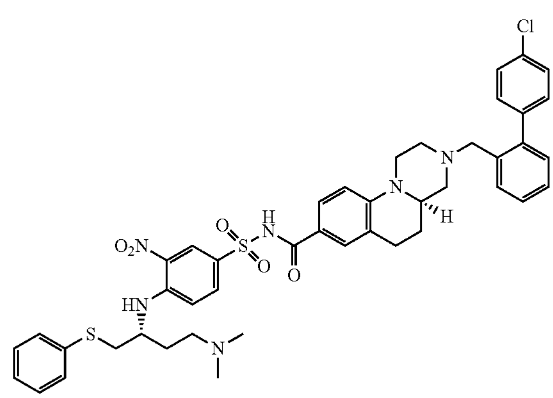 [SMILES: CN(C)CC[C@H](CSc1ccccc1)Nc1ccc(S(=O)(=O)NC(=O)c2ccc3c(c2)CC[C@@H]2CN(Cc4ccccc4-c4ccc(Cl)cc4)CCN32)cc1[N+](=O)[O-]] |

TABLE 1-continued

Suitable Bcl-2 Family Protein Inhibitors

| Trade-name | Chemical Name | Structure |
| --- | --- | --- |
| S64315 (MIK665) | (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[2-(hydroxymethyl)phenyl]pyrimidin-4-yl]methoxy]phenyl]propanoic acid | 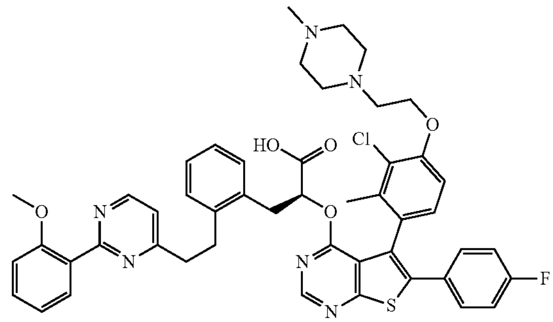 [SMILES: COc1ccccc1-c1nccc(CCc2ccccc2C[C@H](Oc2ncnc3sc(-c4ccc(F)cc4)c(-c4ccc(OCCN5CCN(C)CC5)c(Cl)c4C)c23)C(=O)O)n1] |
| S63845 | α(R)-[[(5S)-5-[3-chloro-2-methyl-4-[2-(4-methyl-1-piperazinyl)ethoxy]phenyl]-6-(5-fluoro-2-furanyl)thieno[2,3-d]pyrimidin-4-yl]oxy]-2-[[1-(2,2,2-trifluoroethyl)-1H-pyrazol-5-yl]methoxy]-benzenepropanoic acid | 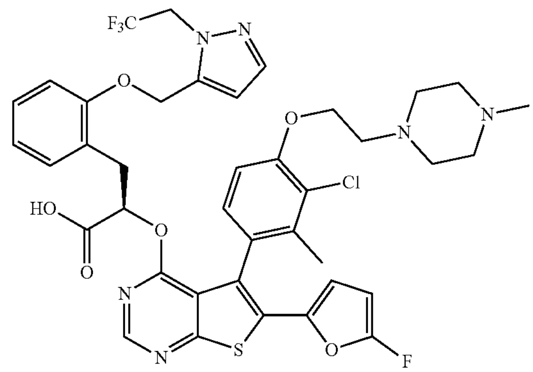 [SMILES: Cc1c(-c2c(-c3ccc(F)o3)sc3ncnc(O[C@H](Cc4ccccc4OCc4ccnn4CC(F)(F)F)C(=O)O)c23)ccc(OCCN2CCN(C)CC2)c1Cl] |
| AMG397; murizatoclax | (3'R,4S,6'R,7'R,8'E,11'S,12'R)-7'-[[(9aR)-1,3,4,6,7,8,9,9a-octahydropyrido[1,2-a]pyrazin-2-yl]methyl]-7'-chloro-7'-methoxy-11',12'-dimethyl-13',13'-dioxospiro[2,3-dihydro-1H-naphthalene-4,22'-20-oxa-13λ$^6$-thia-1,14-diazatetracyclo[14.7.2.0$^{3,6}$.0$^{19,24}$]pentacosa-8,16(25),17,19(24)-tetraene]-15'-one | 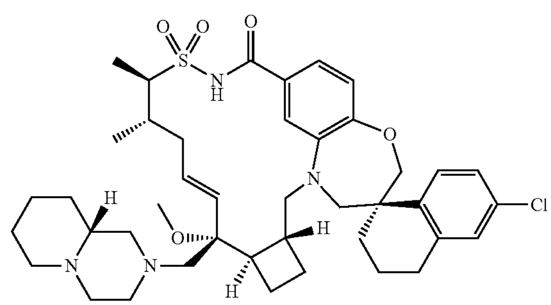 [SMILES: CO[C@]1(CN2CCN3CCCC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] |
| AMG176 | (3'R,4S,6'R,7'S,8'E,11'S,12'R)-7'-chloro-7'-methoxy-11',12'-dimethyl-13',13'-dioxospiro[2,3-dihydro-1H-naphthalene-4,22'-20-oxa-13lambda6-thia-1,14-diazatetracyclo[14.7.2.03,6.019,24]pentacosa-8,16(25),17,19(24)-tetraene]-15'-one | 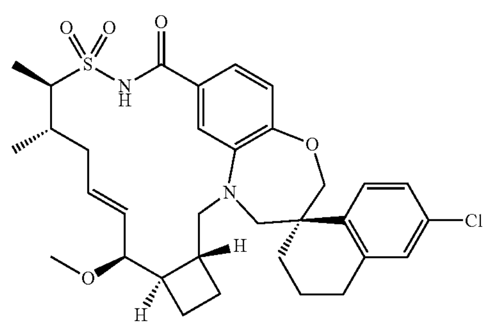 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] |

TABLE 1-continued

Suitable Bcl-2 Family Protein Inhibitors

| Trade-name | Chemical Name | Structure |
|---|---|---|
| AZD5991 | 17-chloro-5,13,14,22-tetramethyl-28-oxa-2,9-dithia-5,6,12,13,22pentazaheptacyclo[27.7.1.14,7.011,15.016,21.020,24.030,35]octatriacontal(36),4(38),6,11,14,16,18,20,23,29(37),30,32,34-tridecaene-23-carboxylic acid | 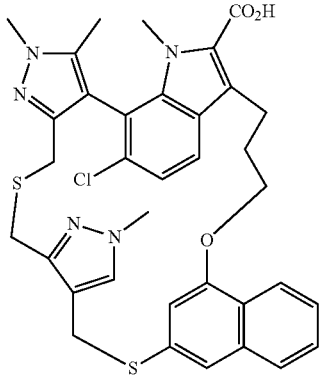 [SMILES: Cc1c2c(nn1C)CSCc1nn(C)cc1CSc1cc(c3ccccc3c1)OCCCc1c(C(=O)O)n(C)c3c-2c(Cl)ccc13] |
| UMI-77 | 2-[4-[(4-bromophenyl)sulfonylamino]-1-hydroxynaphthalen-2-yl]sulfanylacetic acid | 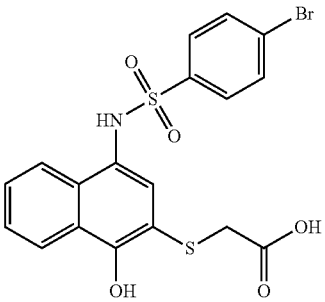 [SMILES: O=C(O)CSc1cc(NS(=O)(=O)c2ccc(Br)cc2)c2ccccc2c1O] |
| A-1210477 | 7-[5-[[4-[4-(dimethylsulfamoyl)piperazin-1-yl]phenoxy]methyl]-1,3-dimethylpyrazol-4-yl]-1-(2-morpholin-4-ylethyl)-3-(3-naphthalen-1-yloxypropyl)indole-2-carboxylic acid | 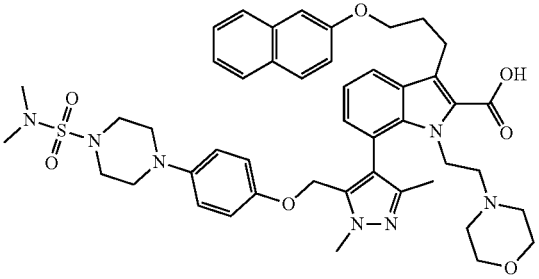 [SMILES: Cc1nn(C)c(COc2ccc(N3CCN(S(=O)(=O)N(C)C)CC3)cc2)c1-c1cccc2c(CCCOc3ccc4ccccc4c3)c(C(=O)O)n(CCN3CCOCC3)c12] |
| Maritoclax; marinopyrrole A | [4,5-dichloro-1-[4,5-dichloro-2-(2-hydroxybenzoyl)-1H-pyrrol-3-yl]pyrrol-2-yl]-(2-hydroxyphenyl)methanone | 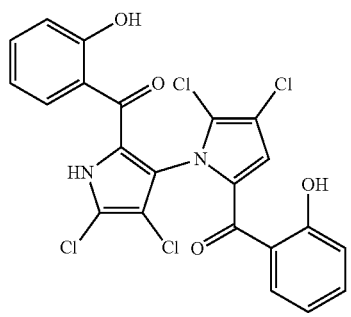 [SMILES: O=C(c1ccccc1O)c1[nH]c(Cl)c(Cl)c1-n1c(C(=O)c2ccccc2O)cc(Cl)c1Cl] |
| BDA-366 | 1-[[(2S)-3-(diethylamino)-2-hydroxypropyl]amino]-4-[[(2S)-oxiran-2-yl]methylamino]anthracene-9,10-dione | 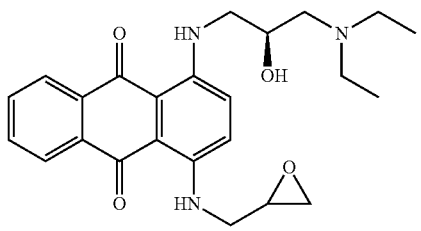 [SMILES: CCN(CC)C[C@@H](O)CNc1ccc(NCC2CO2)c2c1C(=O)c1ccccc1C2=O] |

TABLE 1-continued

Suitable Bcl-2 Family Protein Inhibitors

| Trade-name | Chemical Name | Structure |
|---|---|---|
| Obatoclax; GX15-070 | (2Z)-2-[(5Z)-5-[(3,5-dimethyl-1H-pyrrol-2-yl)methylidene]-4-methoxypyrrol-2-ylidene]indole | |
| Sabutoclax; BI-97CI | 2,3,5-trihydroxy-7-methyl-N-[(2R)-2-phenylpropyl]-6-[1,6,7-trihydroxy-3-methyl-5-[[(2R)-2-phenylpropyl]carbamoyl]naphthalen-2-yl]naphthalene-1-carboxamide | |
| apogossypol | 3-methyl-5-propan-2-yl-2-(1,6,7-trihydroxy-3-methyl-5-propan-2-ylnaphthalen-2-yl)naphthalene-1,6,7-triol | |
| AT101; gossypol | 7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde | |
| antimycin A | [(2R,3S,6S,7R,8R)-3-[(3-formamido-2-hydroxybenzoyl)amino]-8-hexyl-2,6-dimethyl-4,9-dioxo-1,5-dioxonan-7-yl] 3-methylbutanoate | |
| Gambogic Acid | (Z)-4-[(1S,2S,8R,17S,19R)-12-hydroxy-8,21,21-trimethyl-5-(3-methylbut-2-enyl)-8-(4-methylpent-3-enyl)-14,18-dioxo-3,7,20-trioxahexacyclo[15.4.1.02,15.02,19.04,13.06,11]docosa-4(13),5,9,11,15-pentaen-19-yl]-2-methylbut-2-enoic acid | 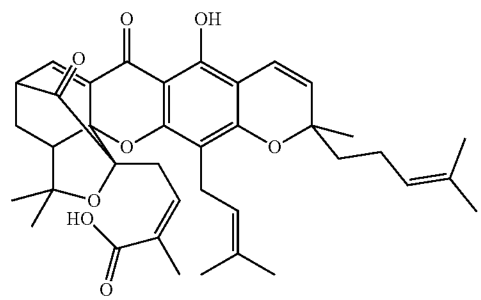 [SMILES: CC(C)=CCCC1(C)C=Cc2c(O)c3c(c(CC=C(C)C)c2O1)OC12C(=CC4CC1C(C)(C)OC2(C/C=C(/C)C(=O)O)C4=O)C3=O] |

In any embodiment of the methods disclosed herein, the Bcl-2 family protein inhibitor may be navitoclax (ABT-263). Navitoclax (ABT-263) functions as a small molecule mimetic of the BH3 domain of the BH3-only sensitizer protein BAD, efficiently binds to BCL-2, BCL-XL, and BCL-W, releasing bound pro-apoptotic proteins and causing MOMP in BCL-2 dependent cancer cells (see, e.g., Pan et al., "Selective BCL-2 Inhibition by ABT-199 Causes On Target Cell Death in Acute Myeloid Leukemia," *Cancer Discov.* 4(3):362-375 (2014)).

In any embodiment, the Bcl-2 family protein inhibitor is venetoclax (ABT-199). Venetoclax (ABT-199) is a modified BH3-mimetic derivative of navitoclax (ABT-263) which maintains specificity for BCL-2, but lacks affinity for BCL-XL (see, e.g., Pan et al., "Selective BCL-2 Inhibition by ABT-199 Causes On Target Cell Death in Acute Myeloid Leukemia," *Cancer Discov.* 4(3):362-375 (2014)).

In any embodiment of the methods disclosed herein, the combination therapy may comprise the MALT1 inhibitor of formula (I) and 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199).

In any embodiment of the methods disclosed herein, the MALT1 inhibitor of formula (I) and the Bcl-2 family protein inhibitor may be administered concurrently or sequentially.

In any embodiment of the methods disclosed herein, the MALT1 inhibitor of formula (I) and the Bcl-2 family protein inhibitor may be administered in a combined dosage form or in separate dosage forms.

In any embodiment of the methods according to the disclosure, an effective amount of a pharmaceutical agent(s) according to the disclosure (i.e., the MALT1 inhibitor having the structure of Formula (I) and the Bcl-2 family protein inhibitor) is administered to a subject suffering from or diagnosed as having such a disease, disorder, or condition (e.g., a malignancy). A "therapeutically effective amount" means an amount or dose sufficient to generally bring about the desired therapeutic benefit in patients in need of such treatment for the designated disease, disorder, or condition. Therapeutically effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An exemplary dose of the compound of Formula (I) of the present disclosure is a dose is in the range of from about 100 mg to 400 mg of the compound of Formula (I) per day, in single or divided dosage units (e.g., BID, TID, QID). An exemplary dose of the Bcl-2 family inhibitor of the present disclosure is a dose is in the range of from about 20 mg to 400 mg of the Bcl-2 family inhibitor per day, in single or divided dosage units (e.g., BID, TID, QID).

In some embodiments, the therapeutically effective amount of the compound of Formula (I) is from about 10 mg to about 1,000 mg. In some embodiments, the therapeutically effective amount of the compound of Formula (I) is from about 10 mg to about 100 mg. In some embodiments, the therapeutically effective amount of the compound of Formula (I) is from about 100 mg to about 200 mg. In some embodiments, the therapeutically effective amount of the compound of Formula (I) is from about 100 mg to about 300 mg. In some embodiments, the therapeutically effective amount of the compound of Formula (I) is from about 100 mg to about 400 mg. In some embodiments, the therapeutically effective amount of the compound of Formula (I) is from about 100 mg to about 500 mg. In some embodiments, the therapeutically effective amount of the compound of Formula (I) is from about 100 mg to about 600 mg. In some embodiments, the therapeutically effective amount of the compound of Formula (I) is from about 100 mg to about 700 mg. In some embodiments, the therapeutically effective amount of the compound of Formula (I) is from about 100 mg to about 800 mg. In some embodiments, the therapeutically effective amount of the compound of Formula (I) is from about 100 mg to about 900 mg. In some embodiments, the therapeutically effective amount of the compound of Formula (I) is from about 100 mg to about 1,000 mg. In some embodiments, the combination therapy comprises about 100 mg to about 400 mg of the MALT1 inhibitor of formula (I). In other embodiments, the combination therapy comprises about 150 mg to about 350 mg of the MALT1 inhibitor of formula (I). In further embodiments, the combination therapeutic comprises about 200 mg to about 300 mg of the MALT1 inhibitor of formula (I).

In some embodiments, the therapeutically effective amount of the compound of Formula (I) is from about 100 mg to 400 mg/day. Thus, in some embodiments, the compound of Formula (I) is administered at a dosage of 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, or 400 mg.

In some embodiments, the combination therapeutic comprises about 20 mg to about 400 mg of the Bcl-2 family protein inhibitor. Thus, in some embodiments, the Bcl-2 family protein inhibitor is administered at a dosage of 20 mg, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, or 400 mg.

In any embodiment of the methods disclosed herein, the dose of the Bcl-2 family protein inhibitor is incrementally increased from about 20 mg/day to about 400/day with repeated administration of said combination therapy to avoid tumor lysis syndrome. For example, in some embodiments, e.g., when the Bcl-2 family protein inhibitor is venetoclax (ABT-199), the Bcl-2 family protein inhibitor may be administered according to a weekly ramp up dosage regimen comprising administering about 20 mg/day for the first week, about 50 mg/day for the second week, about 100 mg/day for the third week, 200 mg/day for the third week, and 400 mg/day for the fourth week and beyond.

In any embodiment of the methods disclosed herein, the combination therapy may be administered once a day, twice a day, or more. For example, the MALT1 inhibitor of formula (I) may be administered twice daily and the Bcl-2 family protein inhibitor may be administered once daily. In some embodiments, the MALT1 inhibitor of formula (I) is administered twice daily for at least 7 days, and once daily thereafter, and the Bcl-2 family protein inhibitor is administered once daily.

In any embodiment of the methods disclosed herein, administering the combination therapy achieves a synergistic effect on tumor growth inhibition as compared to administering the MALT1 inhibitor of formula (I) or the Bcl-2 family protein inhibitor alone.

In any embodiment, the method of the present disclosure involves treating diffuse large B-cell lymphoma (DLBCL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the DLBCL is relapsed or refractory DLBCL.

In any embodiment, the method of the present disclosure involves treating mantle cell lymphoma (MCL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the MCL is relapsed or refractory MCL.

In any embodiment, the method of the present disclosure involves treating follicular lymphoma (FL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the FL is relapsed or refractory FL.

In any embodiment, the method of the present disclosure involves treating transformed follicular lymphoma (tFL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the tFL is relapsed or refractory tFL.

In any embodiment, the method of the present disclosure involves treating marginal zone lymphoma (MZL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the MZL is relapsed or refractory MZL.

In any embodiment, the method of the present disclosure involves treating chronic lymphocytic leukemia (CLL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the CLL is relapsed or refractory CLL.

In any embodiment, the method of the present disclosure involves treating small lymphocytic lymphoma (SLL) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the SLL is relapsed or refractory SLL.

In any embodiment, the method of the present disclosure involves treating Waldenström macroglobulinemia (WM) in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily. In some embodiments, the WM is relapsed or refractory WM.

In any embodiment, the method of the present disclosure involves treating Burkitt lymphoma in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily.

In any embodiment, the method of the present disclosure involves treating hairy cell leukemia in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily.

In any embodiment, the method of the present disclosure involves treating primary central nervous system lymphoma in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily.

In any embodiment, the method of the present disclosure involves treating primary intraocular lymphoma in a subject. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily.

In any embodiment, the method of the present disclosure involves reducing levels of regulatory T cells in a subject having a malignancy. This method comprises administering to the subject: (i) a therapeutically effective dose of about 100 mg to about 400 mg of the MALT1 inhibitor of Formula (I) or a pharmaceutically acceptable salt, hydrate, polymorph, or solvates thereof, where the compound of Formula (I) is optionally administered twice daily for at least 7 days, and once daily thereafter and (ii) a therapeutically effective dose of about 20 mg to about 400 mg of venetoclax once daily.

In some embodiments, the subject may have received at least two prior lines of therapy, including a BTK inhibitor, prior to administration of MALT1 inhibitor of Formula (I) and venetoclax. In some embodiments, the subject may have received Ibrutinib prior to administration of MALT1 inhibitor of Formula (I) and venetoclax. In some embodiments, the subject may have received first line chemotherapy and at least one subsequent line of systemic therapy, including autologous stem cell transplantation (autoSCT), prior to administration of MALT1 inhibitor of Formula (I) and venetoclax. In some embodiments, the subject may have received at least two prior lines of systemic therapy, including a standard anti CD20 antibody, prior to administration of MALT1 inhibitor of Formula (I) and venetoclax. In some embodiments, the subject may have received at least two prior lines of systemic therapy, prior to administration of MALT1 inhibitor of Formula (I) and venetoclax.

Delivery forms of the compositions of the present disclosure may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the disclosure can be provided in the form of tablets or capsules, or as a solution, emulsion, or suspension. To prepare the oral compositions, the compounds may be formulated to yield an oral dosage form suitable for achieving the therapeutic daily doses described above the compounds of formula (I) and the Bcl-2 family protein inhibitor. The suitable dose may be accomplished by dosing once, twice, three, or four times per day.

Oral tablets may include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semisolid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this disclosure may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier.

Compounds of the disclosure can be prepared using the knowledge of one skilled in the art in combination with the present disclosure. For example, compounds of the disclosure can be prepared according to the schemes and examples disclosed in U.S. Pat. Nos. 10,717,745, 10,934,310 and PCT application publication WO2017100662, each of which is hereby incorporated in its entirety.

Another aspect of the present application is directed to a combination therapeutic comprising: (i) a MALT1 inhibitor having the structure of Formula (I)

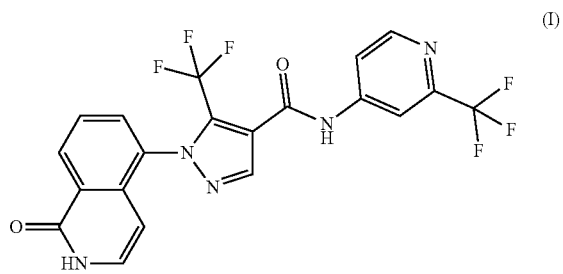

or a pharmaceutically acceptable salt, hydrate, polymorph, or solvates thereof, and (ii) an inhibitor of an anti-apoptotic Bcl-2 family protein.

Suitable Bcl-2 family protein inhibitors are described in more detail supra and include, e.g., 4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide (navitoclax; ABT-263), 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199), N-(4-hydroxyphenyl)-3-[6-[(3S)-3-(morpholin-4-ylmethyl)-3,4-dihydro-1H-isoquinoline-2-carbonyl]-1,3-benzodioxol-5-yl]-N-phenyl-5,6,7,8-tetrahydroindolizine-1-carboxamide; hydrochloride (S55746, BLC201), (2R)-2-[5-[3-chloro-2-methyl-4-[2-(4-methylpiperazin-1-yl)ethoxy]phenyl]-6-(5-fluorofuran-2-yl)thieno[2,3-d]pyrimidin-4-yl]oxy-3-[2-[[2-(2,2,2-trifluoroethyl)pyrazol-3-yl]methoxy]phenyl]propanoic acid (S63845), (3'R,4S,6'R,7'S,8'E,11'S,12'R)-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.0$^{3,6}$.0$^{19,24}$]pentacosa-8,16(25),17,19(24)-tetraene]-15'-one (AMG-176), 17-chloro-5,13,14,22-tetramethyl-28-oxa-2,9-dithia-5,6,12,13,22-pentazahe-ptacyclo[27.7.1.1$^{4,7}$.0$^{11,15}$.0$^{16,21}$.0$^{20,24}$.0$^{30,35}$]octatriaconta-1(36),4(38),6,11,14,16,18,20,23,29(37),30,32,34-tridecaene-23-carboxylic acid (AZD-5991), 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide (ABT-737), 2-[(5E)-5-[(4-bromophenyl)methylidene]-4-oxo-2-sulfanylidene-1,3-thiazolidin-3-yl]-3-methylbutanoic acid (BH3I-1), 7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde (AT101; gossypol), 3-methyl-5-propan-2-yl-2-(1,6,7-trihydroxy-3-methyl-5-propan-2-ylnaphthalen-2-yl)naphthalene-1,6,7-triol (apogossypol), 3-[1-(1-adamantylmethyl)-5-methylpyrazol-4-yl]-6-[8-(1,3-benzothiazol-2-ylcarbamoyl)-3,4-dihydro-1H-isoquinolin-2-yl]pyridine-2-carboxylic acid (A-1331852), 2-[8-(1,3-benzothiazol-2-ylcarbamoyl)-3,4-dihydro-1H-isoquinolin-2-yl]-5-[3-[4-[3-(dimethylamino)prop-1-ynyl]-2-fluorophenoxy]propyl]-1,3-thiazole-4-carboxylic acid (A-1155463), N-[4-(2-tert-butylphenyl)sulfonylphenyl]-2,3,4-trihydroxy-5-[(2-propan-2-ylphenyl)methyl]benzamide (TW-37), 7-[5-[[4-[4-(dimethylsulfamoyl)piperazin-1-yl]phenoxy]methyl]-1,3-dimethylpyrazol-4-yl]-1-(2-morpholin-4-ylethyl)-3-(3-naphthalen-1-yloxypropyl)indole-2-carboxylic acid (A-1210477), 2,3,5-trihydroxy-7-methyl-N-[(2R)-2-phenylpropyl]-6-[1,6,7- trihydroxy-3-methyl-5-[[(2R)-2-phenylpropyl]carbamoyl] naphthalen-2-yl]naphthalene-1-carboxamide (Sabutoclax; BI-97CI), (2R)-2-[5-[3-chloro-2-methyl-4-[2-(4-methylpiperazin-1-yl)ethoxy]phenyl]-6-(4-fluorophenyl)thieno[2,3-d] pyrimidin-4-yl]oxy-3-[2-[[2-[2-(hydroxymethyl)phenyl]pyrimidin-4-yl]methoxy]phenyl]propanoic acid (S64315; MIK665), (3'R,4S,6'R,7'R,8'E,11'S,12'R)-7'-[[(9aR)-1,3,4,6,7,8,9,9a-octahydropyrido[1,2-a]pyrazin-2-yl]methyl]-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.03,6.019,24]pentacosa-8,16(25),17,19 (24)-tetraene]-15'-one (AMG397; murizatoclax), ethyl 2-amino-6-bromo-4-(1-cyano-2-ethoxy-2-oxoethyl)-4H-chromene-3-carboxylate (HA14-1), 2-[4-[(4-bromophenyl)sulfonylamino]-1-hydroxynaphthalen-2-yl]sulfanylacetic acid (UMI-77), [4,5-dichloro-1-[4,5-dichloro-2-(2-hydroxybenzoyl)-1H-pyrrol-3-yl]pyrrol-2-yl]-(2-hydroxyphenyl)methanone (Maritoclax; marinopyrrole A), (2Z)-2-[(5Z)-5-[(3,5-dimethyl-1H-pyrrol-2-yl)methylidene]-4-methoxypyrrol-2-ylidene]indole (Obatoclax; GX15-070), (4aR)-3-[(4'-Chloro [1,1'-biphenyl]-2-yl)methyl]-N-[[4-[[(1R)-3-(dimethylamino)-1-[(phenylthio)methyl]propyl]amino]-3-nitrophenyl]sulfonyl]-2,3,4,4a,5,6-hexahydro-1H-pyrazino[1,2-a] quinoline-8-carboxamide (S44563), [(2R,3S,6S,7R,8R)-3-[(3-formamido-2-hydroxybenzoyl)amino]-8-hexyl-2,6-dimethyl-4,9-dioxo-1,5-dioxonan-7-yl] 3-methylbutanoate (antimycin A), or derivatives thereof.

In any embodiment, the of the combination therapeutic described herein comprises the Bcl-2 family protein inhibitor of 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199). For example, in one embodiment, the combination therapeutic includes the MALT1 inhibitor of formula (I) and 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199).

In some embodiments of the combination therapeutic of the present disclosure, the MALT1 inhibitor of formula (I) and the Bcl-2 family protein inhibitor are formulated together in a single pharmaceutical composition. In other embodiments of the combination therapeutic of the present disclosure, the MALT1 inhibitor of formula (I) and the Bcl-2 family protein inhibitor are formulated as separate pharmaceutical compositions.

In some embodiments of the combination therapeutic of the present disclosure, a dosage unit of the combination therapeutic comprises about 100 mg to about 400 mg of the MALT1 inhibitor of formula (I); about 150 mg to about 350 mg of the MALT1 inhibitor of formula (I); or about 200 mg to about 300 mg of the MALT1 inhibitor of formula (I). Thus, in some embodiments of the combination therapeutic of the present disclosure, a dosage unit of the combination therapeutic comprises a dosage of about 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, or 400 mg of the MALT1 inhibitor compound of formula (I).

In some embodiments of the combination therapeutic of the present disclosure, a dosage unit of the combination therapeutic comprises about 20 mg to about 400 mg of the Bcl-2 family protein inhibitor. Thus, in some embodiments of the combination therapeutic of the present disclosure, a dosage unit of the combination therapeutic comprises a dosage of about 20 mg, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, or 400 mg of the Bcl-2 family protein inhibitor. In some embodiment, the Bcl-2 family protein inhibitor is venetoclax (ABT-199).

The following examples are provided to further describe some of the embodiments disclosed herein. The examples are intended to illustrate, not to limit, the disclosed embodiments. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

According to an embodiment, the invention provides combination therapeutics of MALT1 inhibitor of Formula (I) and an inhibitor of an anti-apoptotic Bcl-2 family protein as described herein.

According to an embodiment, the invention provides combination therapeutics of MALT1 inhibitor of Formula (I) and an inhibitor of an anti-apoptotic Bcl-2 family protein as described herein for use as a medicament.

According to an embodiment, the invention provides combination therapeutics of MALT1 inhibitor of Formula (I) and an inhibitor of an anti-apoptotic Bcl-2 family protein as described herein for the manufacture of a medicament.

According to an embodiment, the invention provides combination therapeutics of MALT1 inhibitor of Formula (I) and an inhibitor of an anti-apoptotic Bcl-2 family protein as described herein for the manufacture of a medicament for the treatment of any one of the disease conditions mentioned herein.

According to an embodiment, the invention provides combinations of MALT1 inhibitor of Formula (I) and an inhibitor of an anti-apoptotic Bcl-2 family protein as described herein for use in the treatment, of diseases or malignancies as described herein.

According to an embodiment, the invention provides combinations of MALT1 inhibitor of Formula (I) and an inhibitor of an anti-apoptotic Bcl-2 family protein as described herein for use in reducing levels of regulatory T cells.

According to an embodiment, the invention provides combinations of MALT1 inhibitor of Formula (I) and an inhibitor of an anti-apoptotic Bcl-2 family protein as described herein for use in the treatment, of diseases or malignancies as described herein, by reducing levels of regulatory T cells.

According to an embodiment, the invention provides combinations of MALT1 inhibitor of Formula (I) and an inhibitor of an anti-apoptotic Bcl-2 family protein as described herein for use in the treatment of a B-cell lymphoma, including but not limited to diffuse large B-cell lymphoma (DLBCL), mantle cell lymphoma (MCL), follicular lymphoma (FL), transformed follicular lymphoma (tFL), marginal zone lymphoma (MZL), chronic lymphocytic leukemia (CLL), small lymphocytic lymphoma (SLL), Waldenström macroglobulinemia (WM), Burkitt lymphoma, hairy cell leukemia, primary central nervous system lymphoma, and primary intraocular lymphoma.

All embodiments described herein for methods for treating, are also applicable for use in treating.

All embodiments described herein for methods for treating a disease or malignancy, are also applicable for use in treating said disease or malignancy.

All embodiments described herein for methods of reducing levels of regulatory T cells in a subject having a disease or malignancy, are also applicable for use in reducing levels of regulatory T cells.

All embodiments described herein for use in treating a disease or malignancy, are also applicable for methods for treating said disease or malignancy.

All embodiments described herein for methods for treating a disease or malignancy, are also applicable for use in a method for treating said a disease or malignancy.

All embodiments described herein for methods of reducing levels of regulatory T cells in a subject having a disease or malignancy, are also applicable for use in a method of reducing levels of regulatory T cells in a subject having a disease or malignancy.

All embodiments described herein for methods of reducing levels of regulatory T cells in a subject having a disease or malignancy, are also applicable for use in a method of reducing levels of regulatory T cells.

All embodiments described herein for use in a method for treating a disease or malignancy, are also applicable for methods for treating said disease or malignancy.

EXAMPLES

Materials and Methods for Examples 1-4

Patient Material

After written informed consent, patient blood was obtained during diagnostic or follow-up procedures at the Departments of Hematology and Pathology of the Academic Medical Center Amsterdam. This study was approved by the AMC Ethical Review Board and conducted in agreement with the Declaration of Helsinki. Blood mononuclear cells of patients with CLL, obtained after Ficoll density gradient centrifugation (Pharmacia Biotech, Roosendaal, The Netherlands) were cryopreserved and stored as previously described (Hallaert et al., "c-Abl Kinase Inhibitors Overcome CD40-mediated Drug Resistance in CLL: Implications for Therapeutic Targeting of Chemoresistant Niches," Blood 112(13):5141-5149 (2008). Expression of CD5 and CD19 (both Beckton Dickinson (BD) Biosciences, San Jose, CA, USA) on leukemic cells was assessed by flow cytometry (FACScanto; BD Biosciences). CLL samples included in this study contained 85-99% $CD5^+/CD19^+$ cells.

Reagents

MALT1 inhibitor (i.e., the MALT1 inhibitor of Formula I) was obtained from Janssen (Beerse, Belgium). Venetoclax was purchased from Active Biochem (Bonn, Germany). S-63845 was purchased from Chemgood (Glen Allen, VA, USA). MG-132 was purchased from Selleckchem (Houston, TX, USA).

Cell Culture and Detection of Apoptosis

Lymphocytes of CLL patients were co-cultured with NIH3T3 fibroblasts stably transfected with human CD40L (3T40) or negative control (3T3) as described before (Urashima et al., "CD40 Ligand Triggered Interleukin-6 Secretion in Multiple Myeloma," Blood 85(7):1903-1912 (1995) and Schultze et al., "CD40-Activated Human B Cells: An Alternative Source of Highly Efficient Antigen Presenting Cells to Generate Autologous Antigen-Specific T Cells for Adoptive Immunotherapy," J. Clin. Invest. 100 (11):2757-2765 (1997). After 24 hours, cells were detached and incubated with or without drugs for an additional 24 hours. CLL cell viability was measured by flow cytometry using DioC6 and TO-PRO-3 viability dyes. Specific apoptosis is defined as [% cell death in treated cells]−[% cell death in medium control]/[% viable cells medium control]× 100%.

Western Blot

Western blot analysis was performed using standard techniques. Membranes were probed with the following antibodies: anti-RelB, p-IκBα, Bcl-XL (Cell Signaling), Bcl10 (Abcam), and actin (Santa Cruz Biotechnology). Odyssey Imager (Li-Cor Biosciences) was used as a detection method according to the manufacturer's protocol.

Proliferation of CLL Cells

CLL PBMCs were labeled with CellTrace Violet and either co-cultured with 3T40 fibroblasts and supplemented with IL-21 (25 ng/mL) or stimulated with CpG ODN2006 (1 μg/mL) and supplemented with IL-2, IL-15, and IL-21 (25 ng/mL). CLL cells were cultured for 5 days. Cells were stained with the following antibodies: CD19-FITC and CD3-APC (BD Biosciences) and CLL cells were gated as single, viable $CD19+/CD3^-$ cells. Samples were measured on a FACS Canto II cytometer (BD Biosciences, San Jose, CA, USA) and proliferation was analyzed using FlowJo software.

Stimulation of CLL Cells

CLL PBMCs were either co-cultured with 3T40 fibroblasts, stimulated with soluble or immobilized anti-IgM (SouthernBiotech, Birmingham, AL, USA) or stimulated with CpG ODN2006 (1 μg/mL) and incubated for 24 hours. Culture supernatant was collected and IL-6, IL-10, and TNFα levels were measured by commercial ELISA kits (Diaclone, Besancon, France). Intracellular flow cytometry staining was performed using Cytofix/Cytoperm according to manufacturer's protocol (BD Biosciences). Cells were stained with the following antibodies: anti-Bcl-XL-FITC, Mcl-1-PE, and Bcl-2-BV421 (BD Biosciences). Samples were measured on a FACS Canto II cytometer (BD Biosciences, San Jose, CA, USA) and analyzed using FlowJo software.

T Cell Stimulation

CLL or healthy donor PBMCs were labeled with CFSE or CTV and stimulated with anti-CD3 (clone 1XE) and anti-CD28 (clone 15E8) antibodies for 4 days. Culture supernatant was collected and IFNγ (ThermoFisher) and TNFα (Diaclone) levels were measured by commercial ELISA kits. The activation/proliferation panel consisted of the following antibodies: CD3-μF700 (eBioscience), CD4-PE-Cy7, CD8-PerCpCy5.5, CD25-APC (BD Bioscience). The differentiation panel consisted of the following antibodies: CD27/CCR7-PerCP-eFluor710 or (eBioscience), CD4-PE-Cy7, CD8-BV786, CD25-PE, CD45RA-BV650, and FoxP3-APC (BD Biosciences). The cytotoxicity panel consisted of the following antibodies: CD107a-FITC (eBioscience), CD4-PerCPeF710, CD8-BV786, CD25-PE, and PD1-PE-Cy7 (BD Biosciences). Samples were measured on a FACS Canto II cytometer (BD Biosciences, San Jose, CA, USA) and analyzed using FlowJo software.

Statistics

The paired sample t-test was used to analyze paired observations. $*p<0.05$; $p<0.01$; $*p<0.001$; $****p<0.0001$.

Example 1—MALT1 Inhibition Affects Downstream NF-κB Signaling in CLL Cells Including Downstream of CD40

Figure 1B:
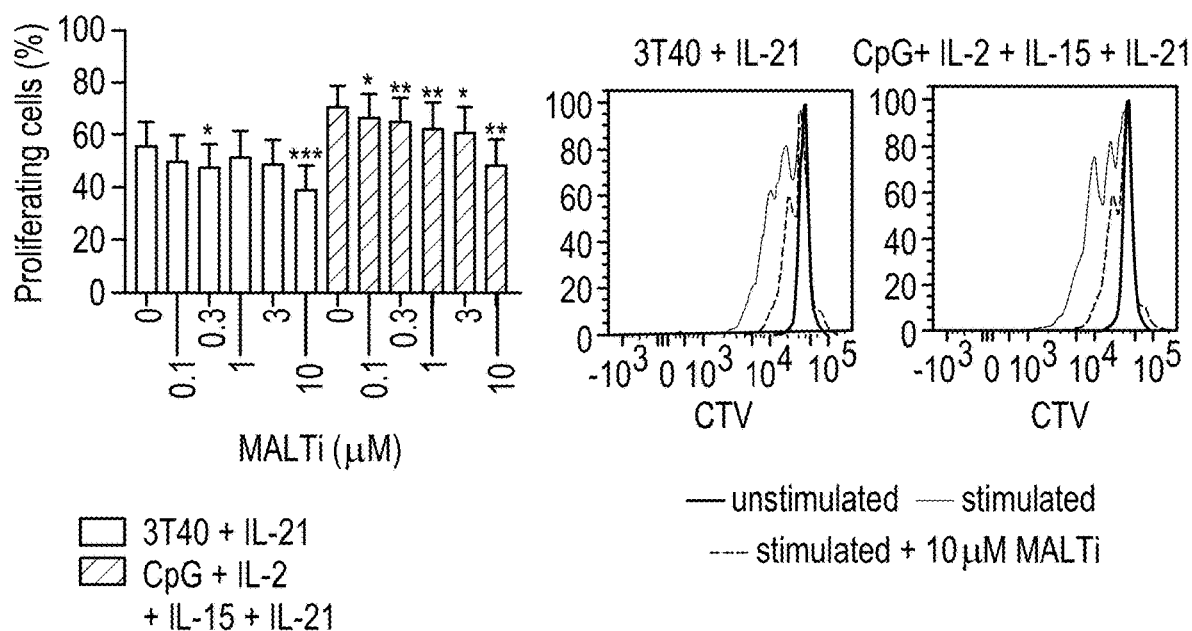
Figure 1C:
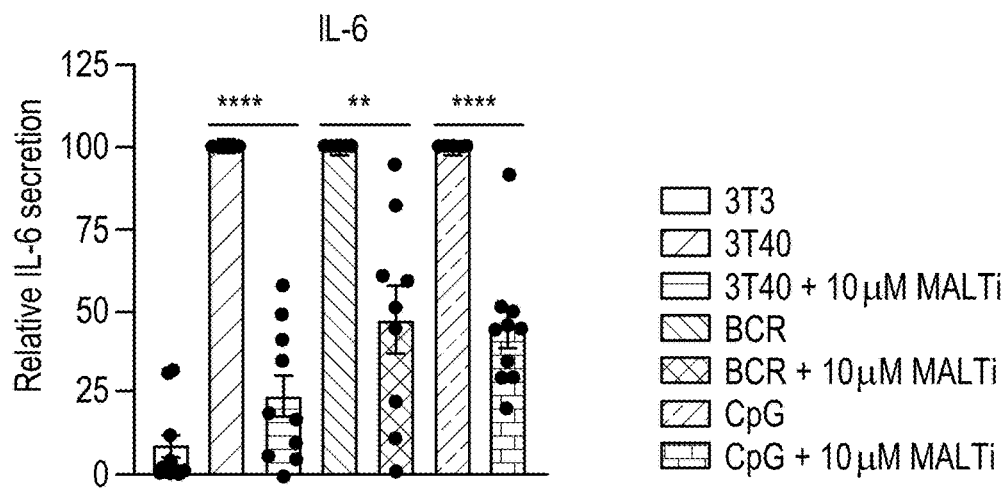
Figure 1D:
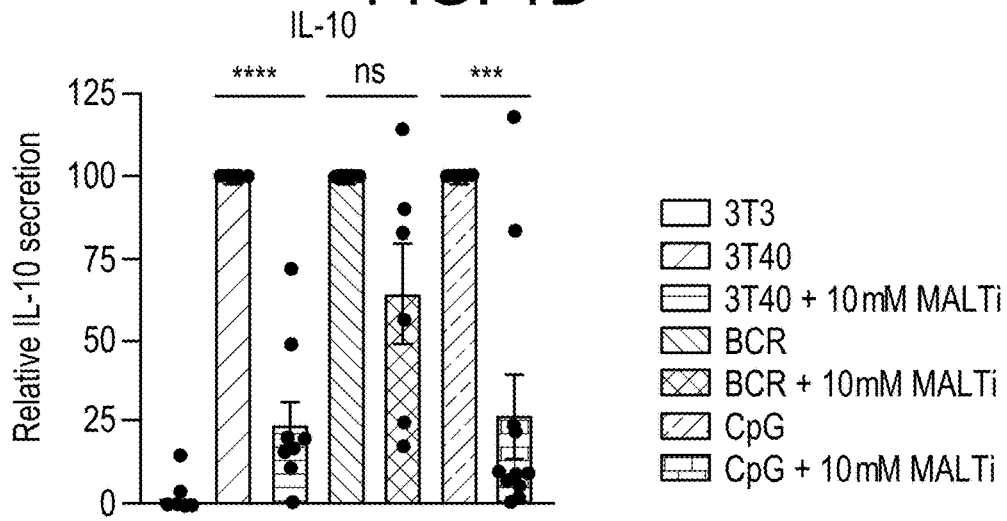
Figure 1E:
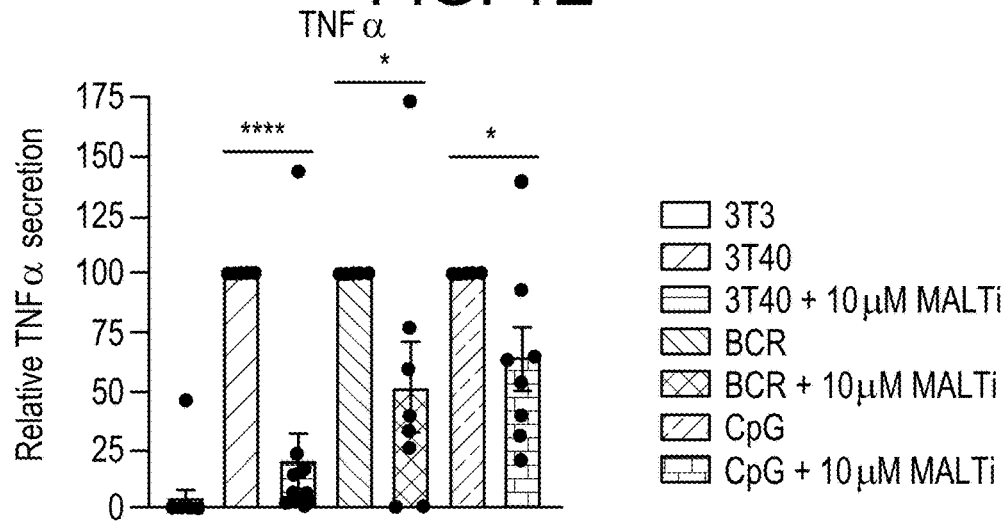
Figure 1F:
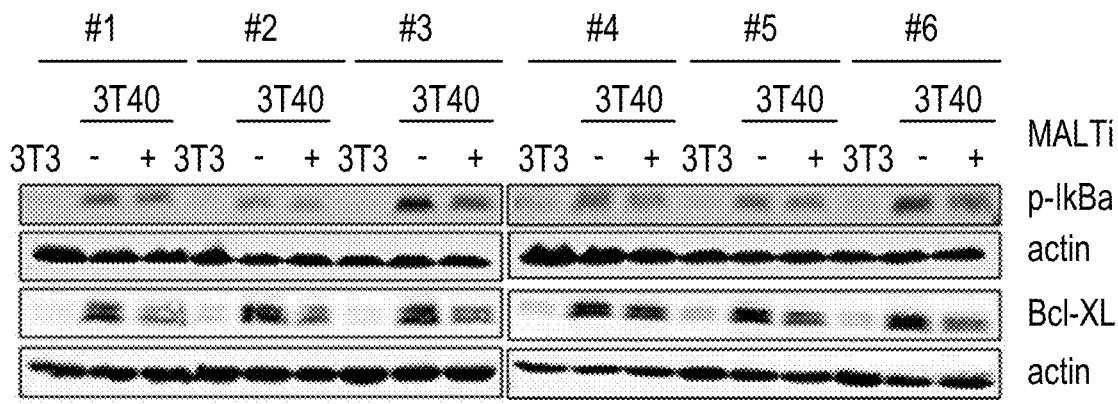
Figure 1G:
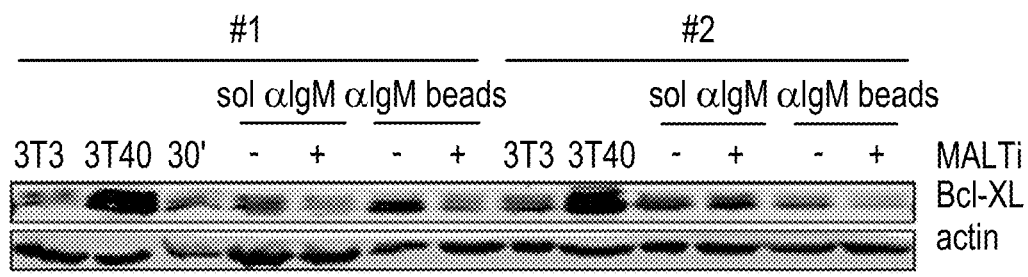
Figure 1H:
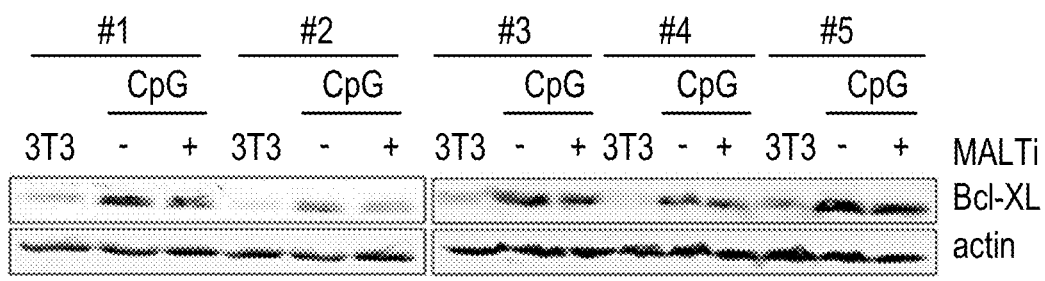
Figure 5:
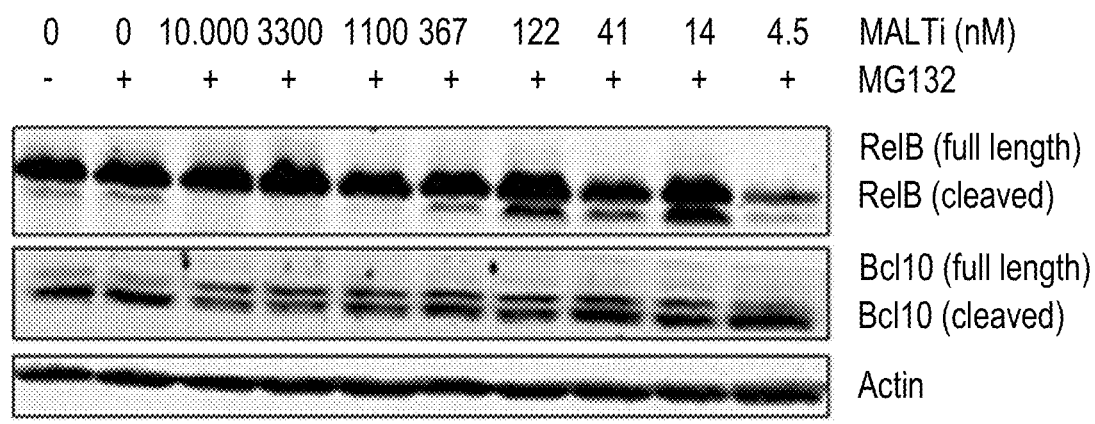
FIG. 5 shows activity of MALT1 inhibitor in OCI-Ly3 cell line, as measured by inhibition of RelB and Bcl10 cleavage by Western blotting. OCI-Ly3 cell lines were cultured for 24 hours in combination with proteasome inhibitor MG132 and indicated concentrations of MALTi. Protein lysates were probed for RelB, Bcl10 and actin or vinculin as loading controls.

First we confirmed activity of the MALT1 inhibitor in the OCI-Ly3 cell line based on inhibition of RelB and Bcl10 cleavage (FIG. 5). To test MALT1 inhibition in the context of CLL, we investigated CLL functionality under divergent microenvironmental stimulations. In contrast to venetoclax, MALT1 inhibition did not induce direct cell death in CLL cells, similar to the BTK inhibitor acalabrutinib (FIG. 1A). Proliferation of CLL cells was induced either via CD40 stimulation in combination with IL-21, or by stimulation with CpG in combination with IL-2, IL-15 and IL-21 (FIG. 1B-C). MALT1 inhibition reduced both types of proliferation but did not fully block the proliferation of CLL cells. Because of the central role of MALT1 in NF-κB signaling, we investigated known targets of NF-κB such as IL-6, IL-10 and TNFα. Both CD40, BCR and TLR9 stimulation induced cytokine secretion of IL-6, IL-10 and TNFα (FIG. 1C-E). MALT1 inhibition resulted in decreased NF-κB-mediated cytokine secretion in all conditions and was most effective in CD40-stimulated cells. The role of MALT1 in the BCR and TLR9 pathway has previously been described, but its role in the CD40 pathway is a new observation. When we further checked for CD40-mediated NF-κB signaling upon treatment with the MALT1 inhibitor, we observed a decrease in p-IκBα and the NF-κB target Bcl-XL, confirming a contribution of MALT1 in CD40 signaling (FIG. 1F). Upon BCR stimulation with soluble or immobilized anti-IgM or TLR9 stimulation via CpG, inhibition of Bcl-XL expression was also observed (FIG. 1G-H). In summary, these results suggest that MALT1 targets downstream NF-κB signaling in CLL not only downstream of the BCR and TLR9, but also in the context of CD40 signaling.

Example 2—MALT1 Inhibition Sensitizes CLL Cells to BH3 Mimetics

Figure 2A:
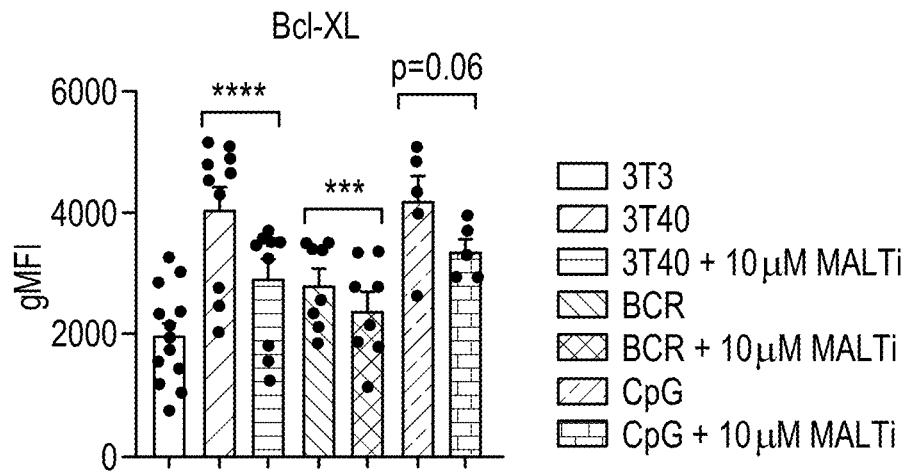
FIGS. 2A-2I demonstrate that MALT1 inhibition sensitizes CLL cells to BH3 mimetics.
Figure 2B:
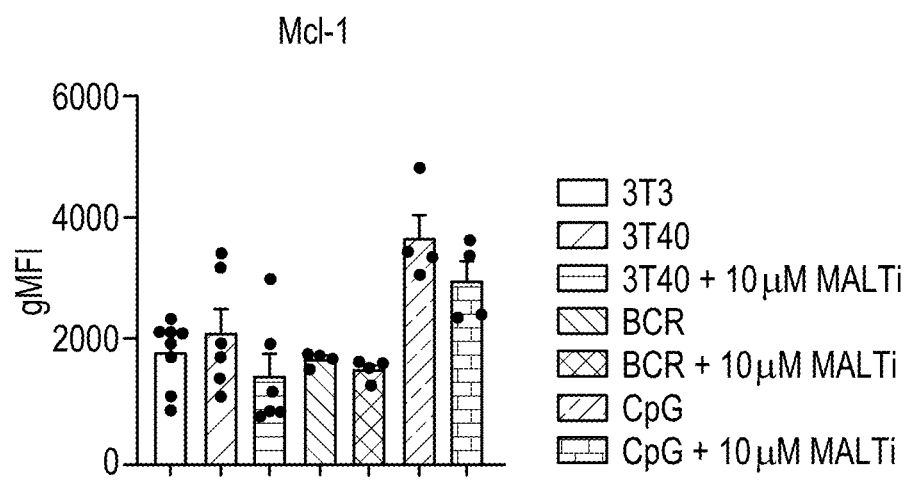
Figure 2C:
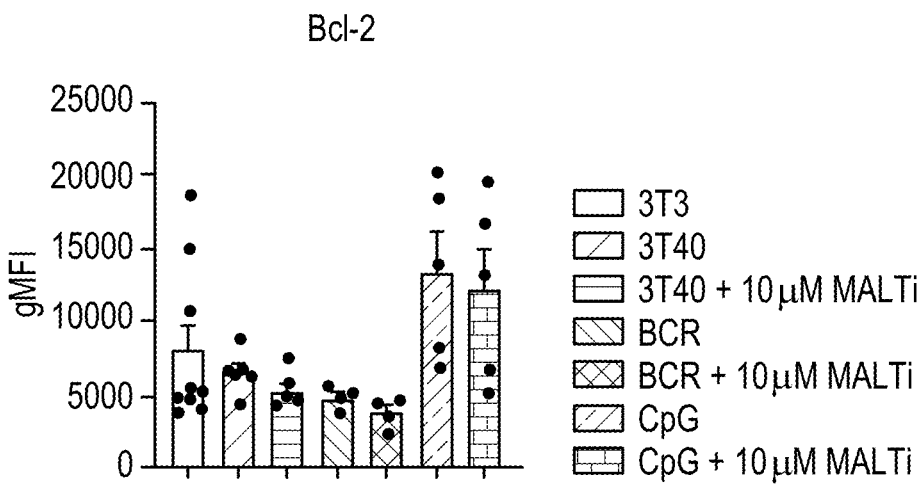
Figure 2D:
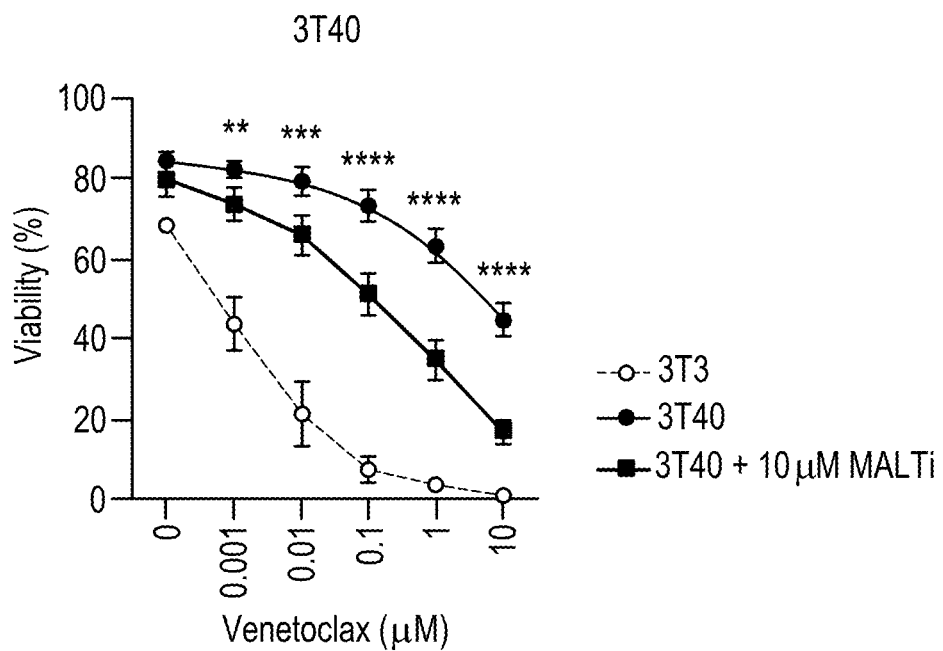
Figure 2E:
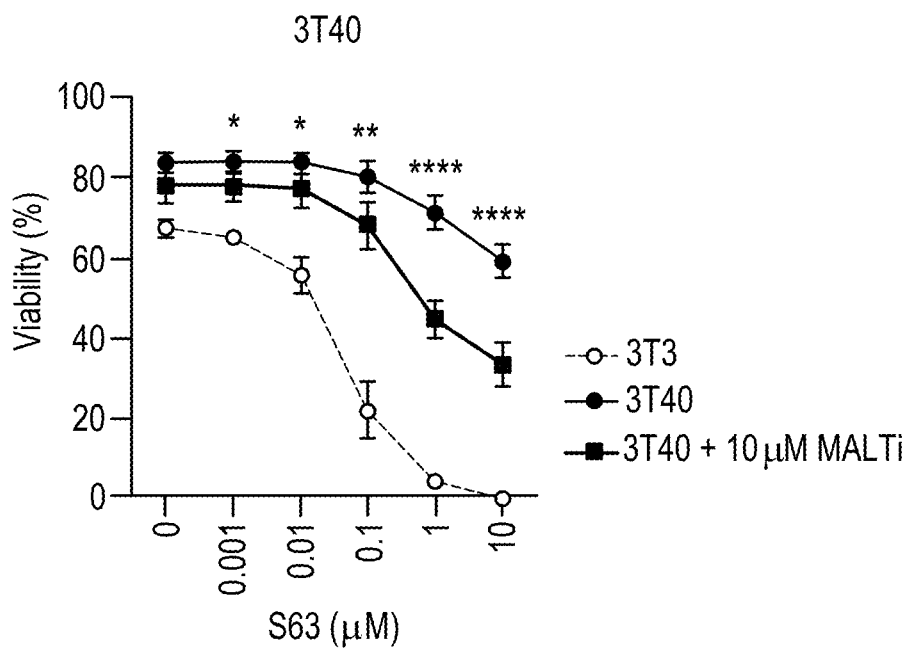
Figure 2F:
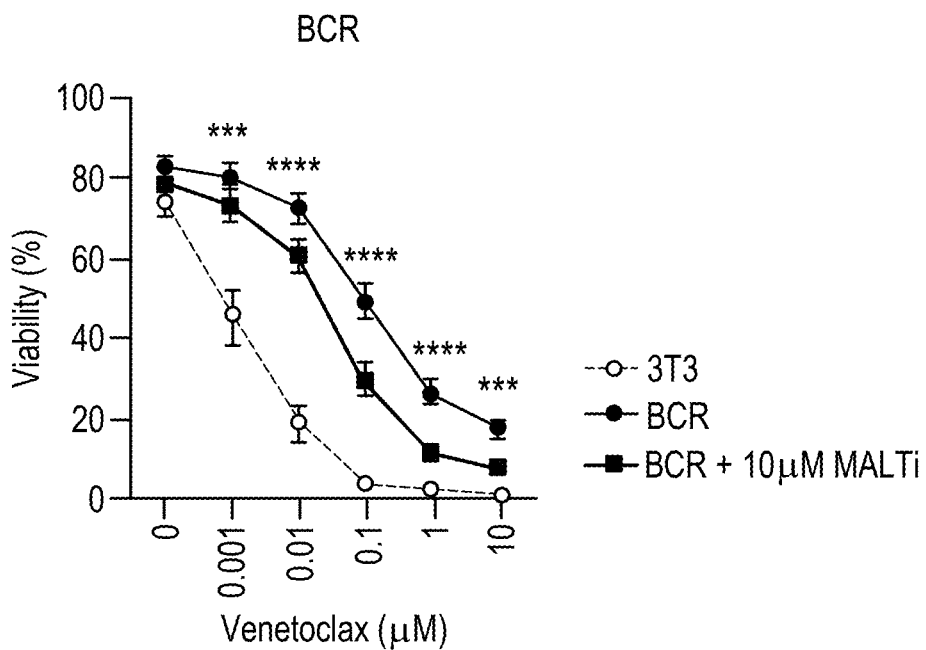
Figure 2G:
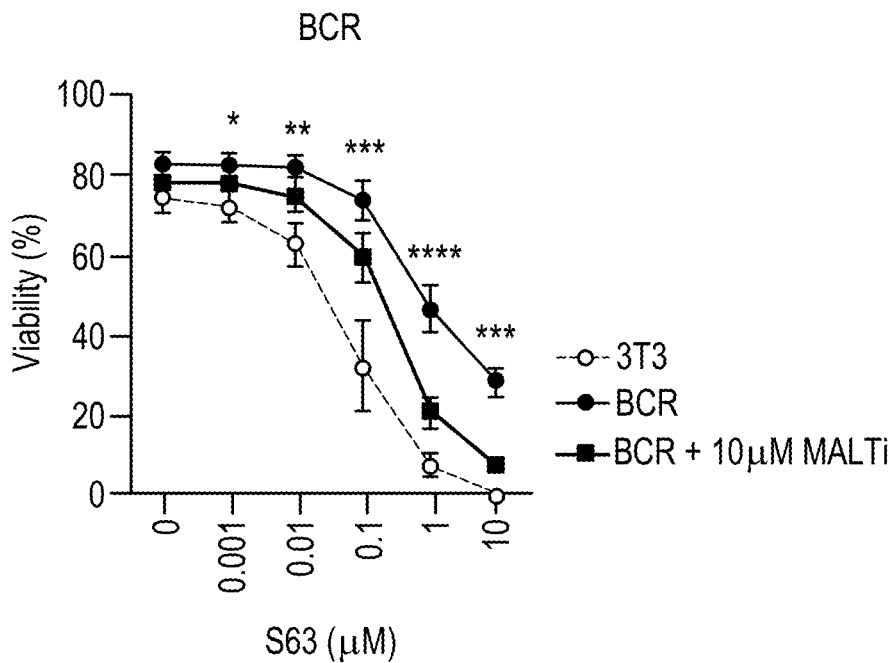
Figure 2H:
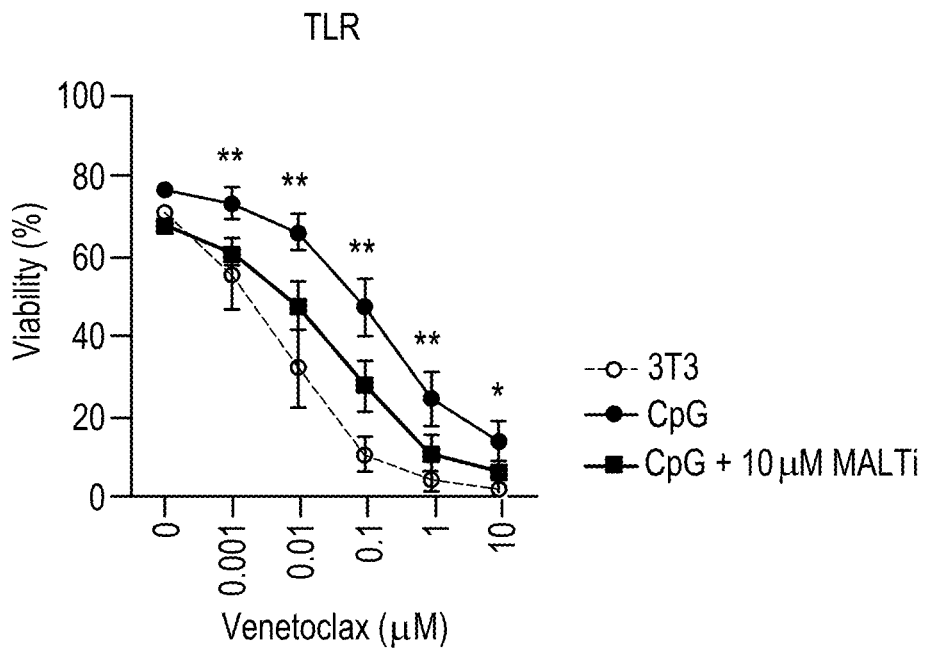
Figure 2I:
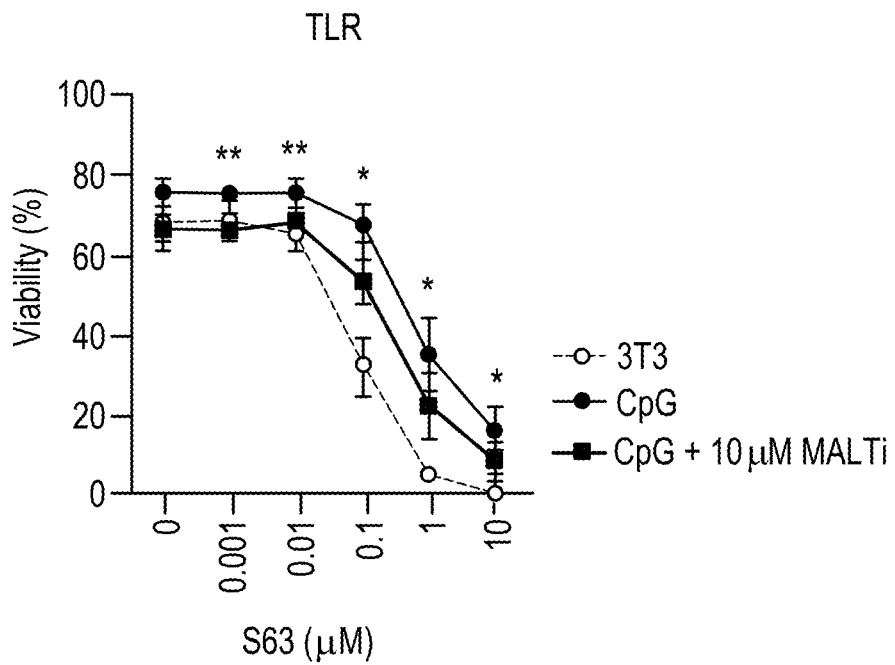

As a result of signals in the lymphoid microenvironment, CLL cells upregulate Bcl-XL, Mcl-1 and Bfl-1 which renders these stimulated CLL cells less sensitive to drugs, in particular the widely used Bcl-2 inhibitor venetoclax. As Bcl-XL expression is mediated by NF-κB signaling MALT1 inhibition could potentially sensitize LN CLL cells to BH3 mimetics via inhibition of Bcl-XL expression. Therefore, we investigated the effect of MALT1 inhibition on the microenvironment-induced drug resistance in CLL cells. First, we measured the expression of Bcl-2 family members Bcl-XL, Mcl-1 and Bcl-2 upon MALT1 inhibition under divergent stimuli. CD40, BCR and TLR9 stimulation all upregulated the expression of Bcl-XL (FIG. 2A-C). Whereas the expression of Bcl-XL was inhibited upon MALT1 inhibition, Mcl-1 and Bcl-2 were not significantly affected (although a trend was evident; more samples need to be evaluated to establish statistical significance). Next, we tested the effect of MALT1 inhibition on the resistance of CLL cells to the Bcl-2 inhibitor venetoclax and the Mcl-1 inhibitor S-63845. Activation of either CD40, BCR or TLR9 signaling induced resistance to both BH3 mimetics (FIG. 2D-I). Concurrent MALT1 inhibition resulted in a shift towards venetoclax and S63 sensitivity in all these conditions. Together, these data suggest that MALT1 inhibition inhibits the expression of Bcl-XL by targeting NF-κB signaling, thereby sensitizing CLL cells in the protective microenvironment to BH3 mimetics.

Example 3—MALT1 Inhibition has Immunomodulatory Effects on T Cells

Figure 3A:
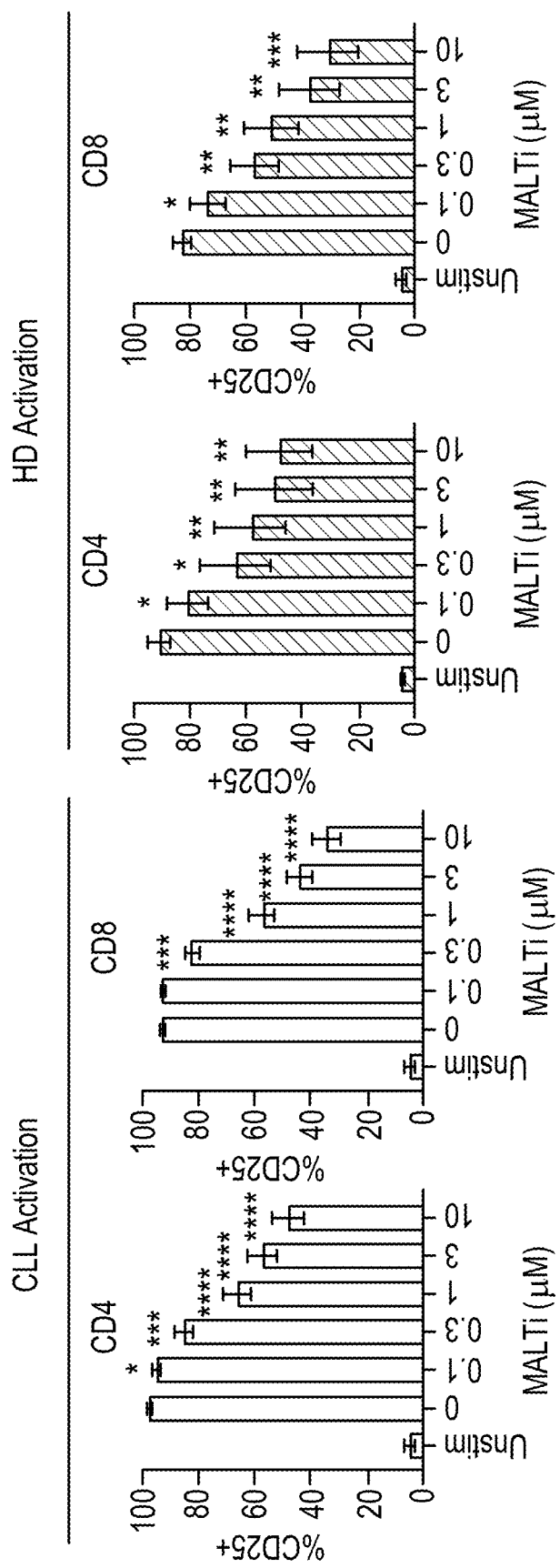
FIGS. 3A-3E demonstrate that MALT1 has immunomodulatory effects on T cells.
Figure 3B:
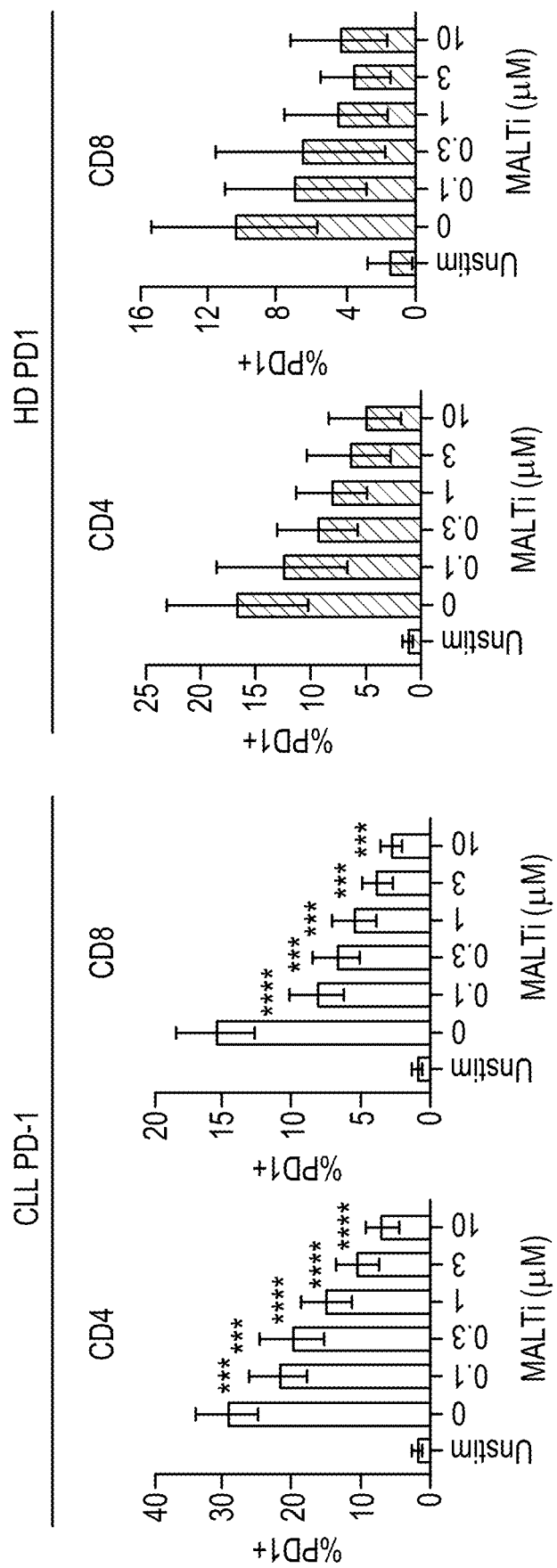
Figure 3C:
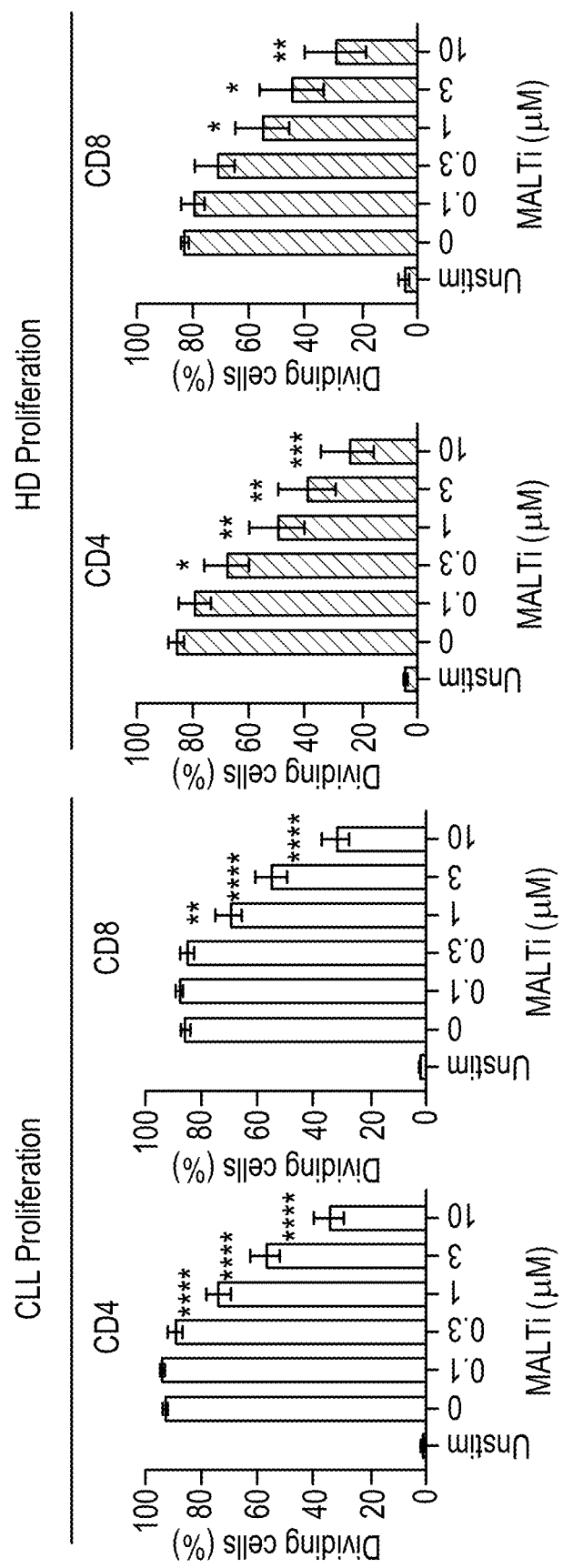
Figure 3D:
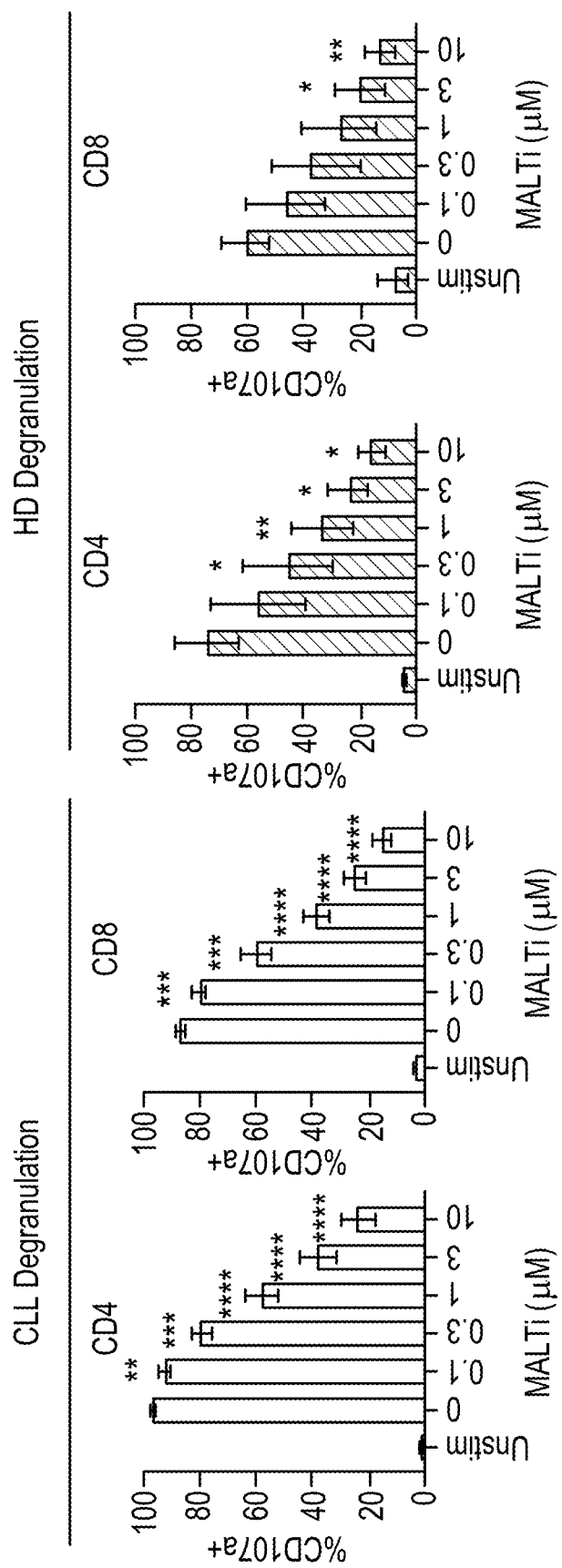
Figure 3E:
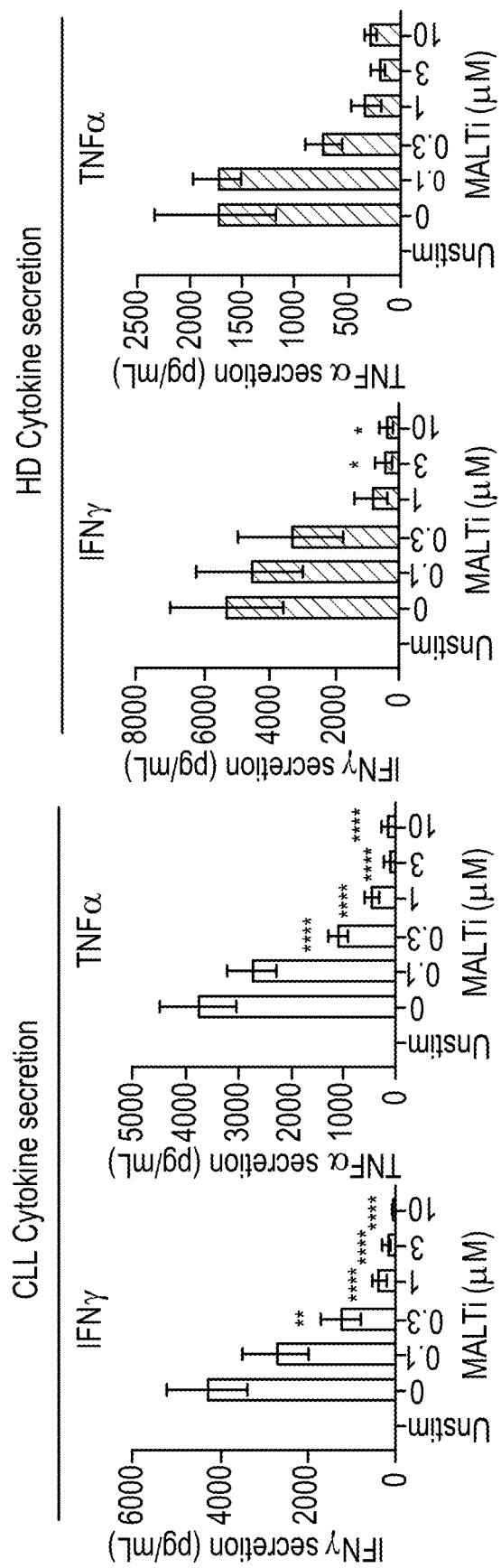

In addition to antigen receptors in B cells, MALT1 also affects signaling downstream of the TCR. Because of the central role of MALT1 in NF-κB signaling, which has been described to be important in the activation of T cells, we investigated the effects of increasing concentrations of the MALT1 inhibitor on T cell activation in both CLL-derived and healthy T cells. Activation and proliferation upon stimulation with soluble anti-CD3/CD28 antibodies was significantly reduced upon MALT1 inhibition in both CD4 and CD8 T cells (FIG. 3A-C). There appeared to be no difference between CLL patients and healthy donors. Additionally, CD107a (LAMP-1) expression as a parameter for T cell degranulation was reduced upon MALT1 inhibition (FIG. 3D). Furthermore, MALT1 inhibition significantly inhibited IFNγ and TNFα cytokine secretion (FIG. 3E). These results suggest that the MALT1 inhibitor impairs various aspects of in vitro T cell activation, when applied at concentrations >1 μM.

Example 4—MALT1 Inhibition Specifically Targets Regulatory T Cells

Figure 4B:
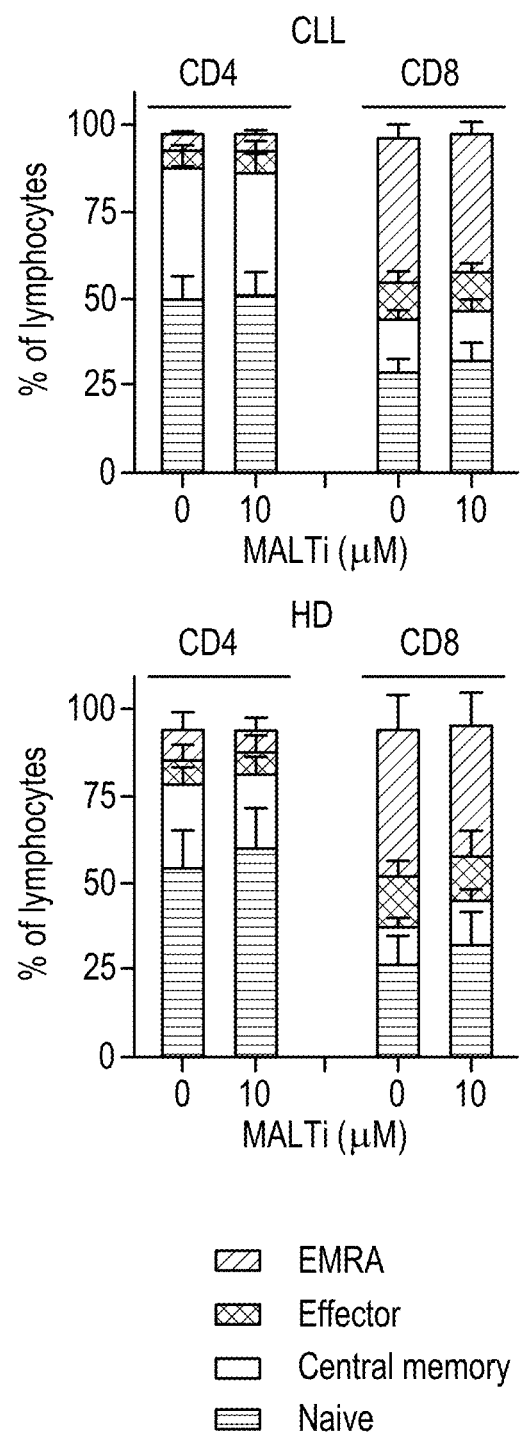
Figure 4C:
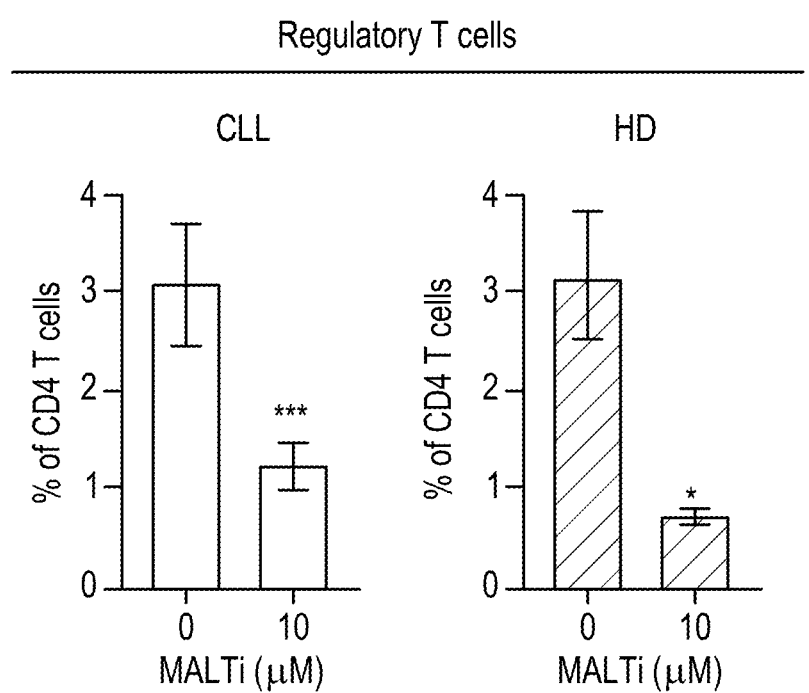

Finally, we tested the effect of MALT1 inhibition on T cell differentiation and subset distribution. Stimulation with anti-CD3/CD28 antibodies induced differentiation of naïve T cells and expanded the effector and central memory T cell pool (FIG. 4A). Treatment with increasing concentrations of MALT1 inhibitor reverted the T cell subset distribution back to the phenotype seen in unstimulated cells, suggesting an inhibition of T cell differentiation. Upon investigation of unstimulated cells, MALT1 inhibition did not affect T cell subset distribution (FIG. 4B). Because of the absence of regulatory T cells in MALT1 knockout mice, we investigated the effect of MALT1 inhibition on the regulatory T cell population in CLL or healthy donor PBMCs. Treatment of unstimulated cells with the MALT1 inhibitor resulted in a specific significant decrease of CD4+/CD25+/FoxP3+ T cells in both CLL and healthy donor samples (FIG. 4C). In summary, these observations suggest that MALT1 inhibition partially inhibits T cell differentiation and specifically targets the regulatory T cell compartment.

Discussion of Examples 1-4

In the context of novel targeted therapies and their toxicities, thorough understanding of the effects of MALT1 inhibition on the function of both healthy and malignant lymphocytes is warranted. MALT1 inhibition could play an important role for the treatment of ibrutinib-resistant CLL, by inhibiting NF-κB signaling downstream of BTK. Our results indicate that CLL cells may be effectively targeted by MALT1 inhibition by interrupting various microenvironmental signaling pathways. Immunomodulatory effects on T cells could also be observed based on T cell activation, differentiation and the depletion of regulatory T cells. Administration of MALT1 inhibitors at clinically relevant concentrations in an in vivo setting will be required to determine whether effects on T cells in combination with the specific depletion of regulatory T cells may shift the pro/anti-inflammatory balance towards enhanced anti-leukemia cytotoxicity.

Treatment with the MALT1 inhibitor did not result in direct cell killing and did not fully block CLL proliferation. There have been conflicting reports of MALT1 knockout on B cell proliferation where some studies show a significant inhibition and others report only minor differences. The effect of MALT1 inhibition on downstream NF-κB activity was more apparent, as we observed a significant inhibition of NF-κB-mediated cytokine secretion, Bcl-XL expression and abrogation of resistance to BH3 mimetics, providing rationale for combination treatment with BH3 mimetics and other cytotoxic agents. Importantly, MALT1 appeared to play a role in both the CD40, BCR and TLR signaling pathways, suggesting that MALT1 inhibition may be an effective approach to negate several key signals in the CLL microenvironment. Although many studies have shown that the proteolytic activity of MALT1 contributes to NF-κB signaling, studies applying MALT1 inhibition reported a partial NF-κB inhibition as opposed to a full blockade. This is consistent with our data and is likely due to the scaffold function of MALT1 which also promotes NF-κB signaling. Further studies could test the efficacy of MALT1 inhibition in ibrutinib-resistant and non-responsive patient samples. To this end, additional readouts are being optimized such as migration and adhesion assays, both processes which have been shown to be strongly dependent on BTK. Additionally, experiments could be carried out in parallel with established BTK inhibitors to evaluate if this treatment strategy may have clinical utility.

Furthermore, we observed decreased T cell activation and proliferation upon stimulation with anti-CD3/CD28 antibodies and concurrent treatment with the MALT1 inhibitor, which is consistent with studies in MALT1 knockout mice. We also observed decreased degranulation parameters and cytokine secretion upon MALT1 inhibition. Upon stimulation with anti-CD3/CD28, T cell differentiation was partially inhibited using higher concentrations of the MALT1 inhibitor. Compared to the strong functional effects of MALT1 inhibition on T cells, this effect on differentiation may likely be the result of impaired T cell activation rather than a block in differentiation. Since T cells in CLL are skewed towards differentiated effector cells, MALT1 inhibition could potentiate T cell-mediated immunity in CLL patients. Additionally, inhibition of MALT1 specifically targeted and depleted the CD4+/CD25+/FoxP3+ T cell pool. The dependency of regulatory T cells on MALT1 has been apparent from many MALT1 mouse models, including MALT1 knockout[39], knockin[20], proteolytic mutants as well as self-cleavage mutants, in which T regulatory numbers were significantly reduced.

Although small molecule inhibitors targeting MALT1 show no severe side effects in mice, mouse models expressing catalytically inactive MALT1 show a hyperinflammatory phenotype with signs of autoimmunity. This difference could be explained by a divergent dependency of signaling events throughout lymphocyte development. In this regard, established MALT1 mouse models may not reflect the actual therapeutic risks of MALT1 inhibitor administration to patients and an inducible mouse model of MALT1 proteolytic activity should be characterized. Our in vitro data suggest immunomodulatory effects of MALT1 inhibition on T cells which are in contrast to a hyperinflammatory phenotype, although a reduction of the regulatory T cell compartment may shift the inflammatory balance and potentially lead to increased antitumor immunity. Moreover, CLL patients have an impaired immune system which is mediated by regulatory T cells, so the selective depletion of regulatory T cells as a result of MALT1 inhibition could potentiate T cell therapies in CLL. In order to further investigate these aspects, pharmacological MALT1 inhibition could be tested in the adoptive transfer TCL1 CLL mouse model. Phase 1 clinical trials assessing the safety and efficacy of the MALT inhibitor applied here, were initiated in 2019 (NCT03900598). The main purpose of that study is to investigate the potential side effects, pharmacokinetics and pharmacodynamics in patients with B cell non-Hodgkin's lymphoma and CLL. Additionally, a phase 1b clinical trial is being undertaken (NCT04876092) where B cell non-Hodgkin's lymphoma and CLL patients will be treated with the MALT inhibitor in combination with the BTK inhibitor ibrutinib.

In conclusion, we show that MALT1 inhibition is able to inhibit multiple pro-survival stimuli in CLL cells in the context of the lymphoid microenvironment. The observed impact of MALT1 inhibition on T cell function and cytotoxicity may either complicate or support treatment in CLL patients, as a reduction of regulatory T cells may promote antitumor immunity in vivo. In vivo studies should further investigate antitumor immunity and the immunomodulatory effects of MALT1 targeting in the context of CLL.

Materials and Methods for Example 5

Animals and Housing

Female NOD/SCID mice were supplied from Shanghai Lingchang Biotechnology Co., Ltd. (Shanghai, China). Mice were 6-8 weeks old at study initiation and were housed in polysulfone IVC cages (325 mm×210 mm×180 mm) at a density of up to 5 mice per cage. Mice were fed a standard rodent chow diet, irradiated, ad libitum and had access to 0.2 mm filtered, reverse osmosis (RO) water.

Experimental Design

The Malt1 inhibitor (Formula I) and Venetoclax in vivo efficacy study design in OCI-LY3 model is set forth in Table 2 below.

TABLE 2

Experimental Design - Treatment Groups and Dosing

| Group | No. | Treatment | Dosing Level (mg/kg) | Dosing Solution (mg/ml) | Dosing Volume (μL/g) | Route of Administration (ROA) | Dosing Frequency & Duration |
|---|---|---|---|---|---|---|---|
| 1 | 8 | Vehicle | — | | 5 | PO | BID |
| 2 | 8 | Venetoclax | 40 | 4 | 10 | PO | QD |
| 3 | 8 | MALT1 inhibitor of Formula I | 30 | 20 | 5 | PO | QD |
| 4 | 8 | MALT1 inhibitor of Formula I | 100 | 20 | 5 | PO | QD |
| 5 | 8 | Venetoclax/MALT1 inhibitor of Formula I | 40/30 | 4/20 | 10/5 | PO | QD/BID |
| 6 | 8 | Venetoclax/MALT1 inhibitor of Formula I | 40/100 | 4/20 | 10/5 | PO | QD/BID |

Note:
1. No.: number of animals per group;
2. Randomization on day 0 after 19 days of the tumor inoculation. Dosing started on the same day of randomization (day 0). For BID dose groups, drug was administrated only once on the day of randomization;
3. All of groups were treated for continuous 17 days, and then were taken down and sample collection performed as requested by client;
4. PO: oral inoculation; BID: twice a day; QD: Once a day.

Drug Formulation

The drug formulations evaluated are set forth in Table 3 below.

TABLE 3

Drug Formulation

| Compound | Preparation Instruction | Concentration (mg/mL) | Storage Condition | Preparation Frequency |
|---|---|---|---|---|
| Vehicle | PEG400 (Acres, Sigma) + PVPVA (90:10) (BASF Kollidon VA) | — | 4° C. | Once per 3 days |
| MALT1 inhibitor of Formula I | PEG400 (Acres, Sigma) + PVPVA (90:10) (BASF Kollidon VA) | 6/20 | 4° C. | Weekly |
| Venetoclax | 60% phosal 50 propylene glycol (PG), 30% polyethylene glycol (PEG) 400 and 10% ethanol | 4 | 4° C. | Once per 3 days |

*Ensure that formulation is mixed immediately before use by gently inverting the tube.

Tumor Inoculation

Tumor fragments from stock mice were harvested and used for inoculation into mice. Each mouse was inoculated subcutaneously in the right front/rear flank with primary human tumor xenograft model tumor fragment (2-3 mm in diameter) for tumor development.

Randomization and Test Article Administration

The randomization was started when the mean tumor size reached 131 mm$^3$. Randomization was performed based on "Matched distribution" method/"Stratified" method (StudyDirector™ software, version 3.1.399.19)/randomized block design. The date of randomization was denoted as day 0. The treatment was initiated on the same day of grouping (day 0) per study design.

Observation and Data Collection

After tumor cell inoculation, the animals were checked daily for morbidity and mortality. During routine monitoring, the animals were checked for any effects of tumor growth and treatment on behavior such as mobility, food and water consumption, body weight gain/loss (Body weights would be measured twice per week after randomization), eye/hair matting, and any other abnormalities. Mortality and observed clinical signs were recorded for individual animals in detail.

Tumor volumes were measured twice per week after randomization in two dimensions using a caliper, and the volume was expressed in mm$^3$ using the formula: V=(L× W×W)/2, where V is tumor volume, L is tumor length (the longest tumor dimension) and W is tumor width (the longest tumor dimension perpendicular to L). Dosing as well as tumor and body weight measurements were conducted in a Laminar Flow Cabinet.

The body weights and tumor volumes were measured by using StudyDirector™ software (version 3.1.399.19).

Criteria for Dosing Holiday and Supplemental Gel Administration

Dosing Holiday. After one measurement of body weight loss (BWL)>20%, the individual mouse would be sacrificed. BWL is calculated based on the BW of mouse on the first day of treatment. After one measurement of BWL>15%, dosing holidays would be given to all the mice in the same group, so all mice within a group are treated the same, treatment would resume when the BWL has recovered to BWL<10%.

Supplemental Gel Administration. Supplemental gel (ClearH2O, Portland, ME, USA) would be supplied to all the animals, if >10% mean BWL is observed in the vehicle group. Note: 1. BWL is calculated based in the BW of mouse on the first day of treatment; 2. Which kind of supplemental gel would be at veterinarian's discretion based on the specific situation of animals 3. Additional fees might be applied according to the amount of supplemental gel used.

Examination of Tumor Growth and Detection of Cytokine Secretion

Study Endpoints. Tumor growth inhibition (TGI): TGI % is an indication of antitumor activity and expressed as: TGI (%)=100×(1−T/C). T and C are the mean tumor volume (or weight) of the treated and control groups, respectively, on a given day. Statistical analysis of the difference in mean tumor volume among the groups was conducted using the methods below.

Study Termination. The study was terminated when the mean tumor burden of the vehicle treated control group reaches 2000 mm$^3$ or one week following the final dose, whichever comes first. The treatment had been performed for 13 days, and there was no extension of the treatment, the study was terminated on day 12 as per request.

Humane Endpoints.

1. Body Weight Loss. The body weight of all animals was monitored throughout the study and animals would be euthanized if they lose over 20% of their body weight relative to the weight at the first day of treatment.
2. Tumor Size. Individual mouse with tumor volume exceeding 3000 mm$^3$ (Sacrifice the individual mouse), or MTV of a group >2000 mm$^3$ (Sacrifice all the mice in the same group).
3. Tumor Appearance Monitoring. To deter cannibalization, any animal exhibiting an ulcerated or necrotic tumor would be separated immediately and singly housed and monitored daily before the animal was euthanized or until tumor regression was complete. Mouse with tumor ulceration of approximately 25% or greater on the surface of the tumor would be euthanized.
4. General Animal Welfare Surveillance. Severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice.

Tumor and Serum Samples Collection on Study Termination. Whole blood samples were collected from all groups at 6 hours post the final dose. Serum samples were isolated from all groups were collected and stored at −80° C. Tumor tissues were collected from all of groups when study was terminated, and split into 2 pieces, take weights, processed to snap frozen and stored in 2 separated tubes.

Tumor and Serum Samples Collection on Study Termination. NF-κB signaling regulates the secretion of multiple cytokines, including interleukin (IL)-6 and IL-10. Secretion of the cytokines (IL-10, TNF-α, IL12p70, and IL-6) in serum samples of OCI-LY3 animals was measured by using a Mesoscale assay (MSD). For in vivo efficacy study, serum samples were isolated from all tumor bearing mice at 6 hours post the final dose of the MALT1 inhibitor of Formula I. For in vivo Pharmacodynamic (PD) experiment, serum samples were isolated from all tumor bearing mice (tumor volume around 700 mm3) at 8 hours post treatment with the MALT1 inhibitor of Formula I (BID dosing). Serum samples were transferred to an MSD plate (V-Plex Proinflammation Panel 1 [human] kit) and incubated for 2 hours at RT followed by a 2-hour incubation with cytokine antibody solution. Plates were read on a SECTOR imager.

Statistical Analysis. To compare tumor volumes of different groups at a pre-specified day, Bartlett's test was first used to check the assumption of homogeneity of variance across all groups. When the p-value of Bartlett's test was >=0.05, one-way ANOVA was run to test overall equality of means across all groups. If the p-value of the one-way ANOVA was <0.05, post hoc testing was further performed by running Tukey's HSD (honest significant difference) tests for all pairwise comparisons, and Dunnett's tests for comparing each treatment group with the vehicle group. When the p-value of Bartlett's test was <0.05, Kruskal-Wallis test was run to test overall equality of medians among all groups. If the p-value the Kruskal-Wallis test was <0.05, post hoc testing was further performed by running Conover's non-parametric test for all pairwise comparisons or for comparing each treatment group with the vehicle group, both with single-step p-value adjustment.

In addition, pairwise comparisons were performed without multiple comparison correction and nominal/uncorrected p-values were reported directly from Welch's t-test or Mann-Whitney U test. Specifically, Bartlett's test was first used to check the assumption of homogeneity of variance for a pair of groups. When the p-value of Bartlett's test was ≥0.05, Welch's t-test was run, otherwise a Mann-Whitney U test was run, to obtain nominal p-values.

All statistical analyses had been done in R-a language and environment for statistical computing and graphics (version 3.3.1). All tests were two-sided unless otherwise specified, and p-values of <0.05 were regarded as statistically significant.

Example 5—In Vivo Efficacy and Pharmacodynamic Marker Summary in OCI-LY3

Figure 6A:
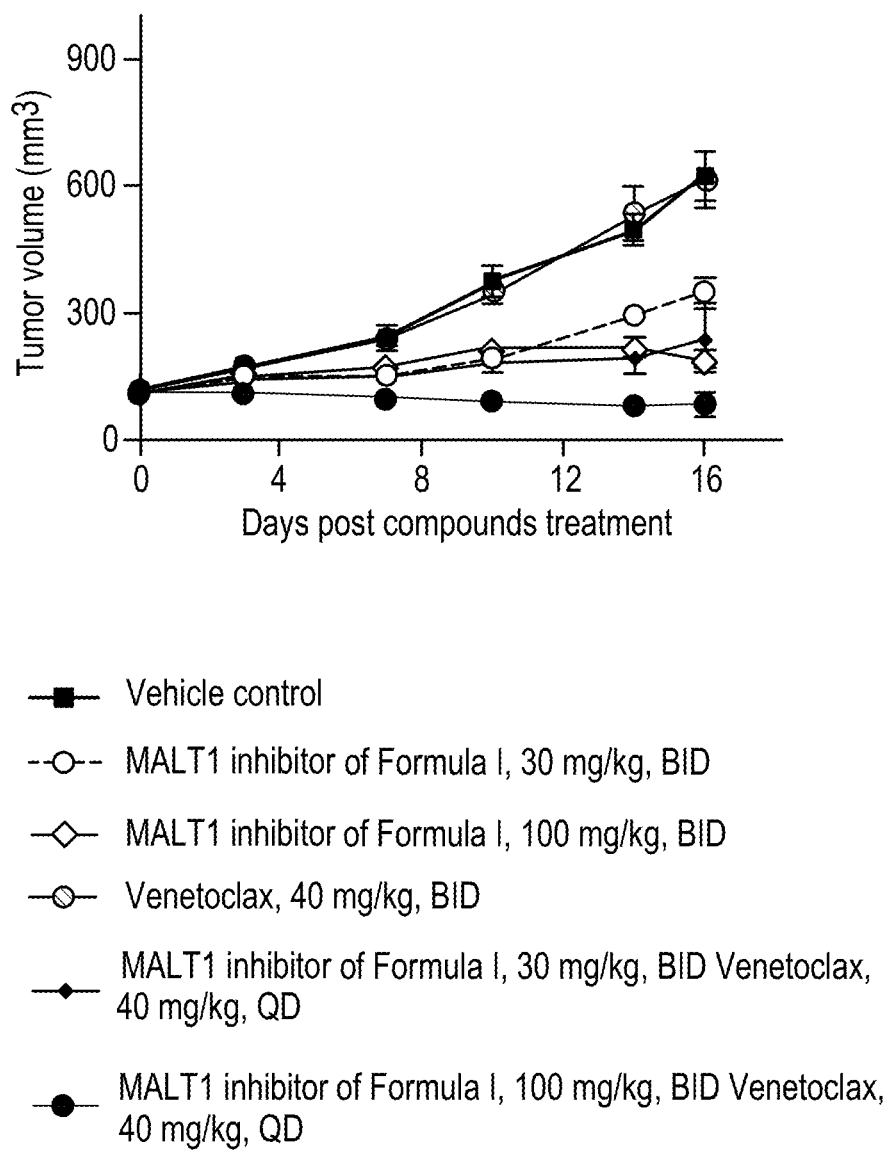

When the BCL2 inhibitor Venetoclax and the MALT1 inhibitor of Formula I were orally administrated to OCI-LY3 tumor bearing mice at dose level 40 mg/kg QD and 30/100 mg/kg BID respectively, they showed in vivo efficacy with tumor growth inhibition (TGI) of 0.98 (P>0.05) and 41.31%, (p<0.001) and 69.92% (p<0.001) respectively at 12 days post treatment (FIG. 6A; Table Z3). The combination therapy of Venetoclax and the MALT1 inhibitor of Formula I (30/100 mg/kg) showed significant in vivo efficacy with TGI of 61.13% and 95.74% (P<0.001) (FIG. 6A; Table 4). Body weight in tumor bearing mice was compared from days 0 to 16 days post treatment (FIG. 6B).

TABLE 4

Tumor Growth Inhibition (TGI) 16-day post treatment with Venetoclax and the MALT1 inhibitor of Formula 1 in OCI-LY3 Models.

| Group | TGI | P value (Treatment arm vs. Vehicle arm) |
|---|---|---|
| MALT1 inhibitor of Formula 1, 30 mg/kg, BID | 41.31 | 2.16e−04 |
| MALT1 inhibitor of Formula 1, 30 mg/kg, BID | 69.92 | 7.63e−10 |
| Venetoclax 40 mg/kg, QD | 0.98 | n.s. |

Figure 6C:
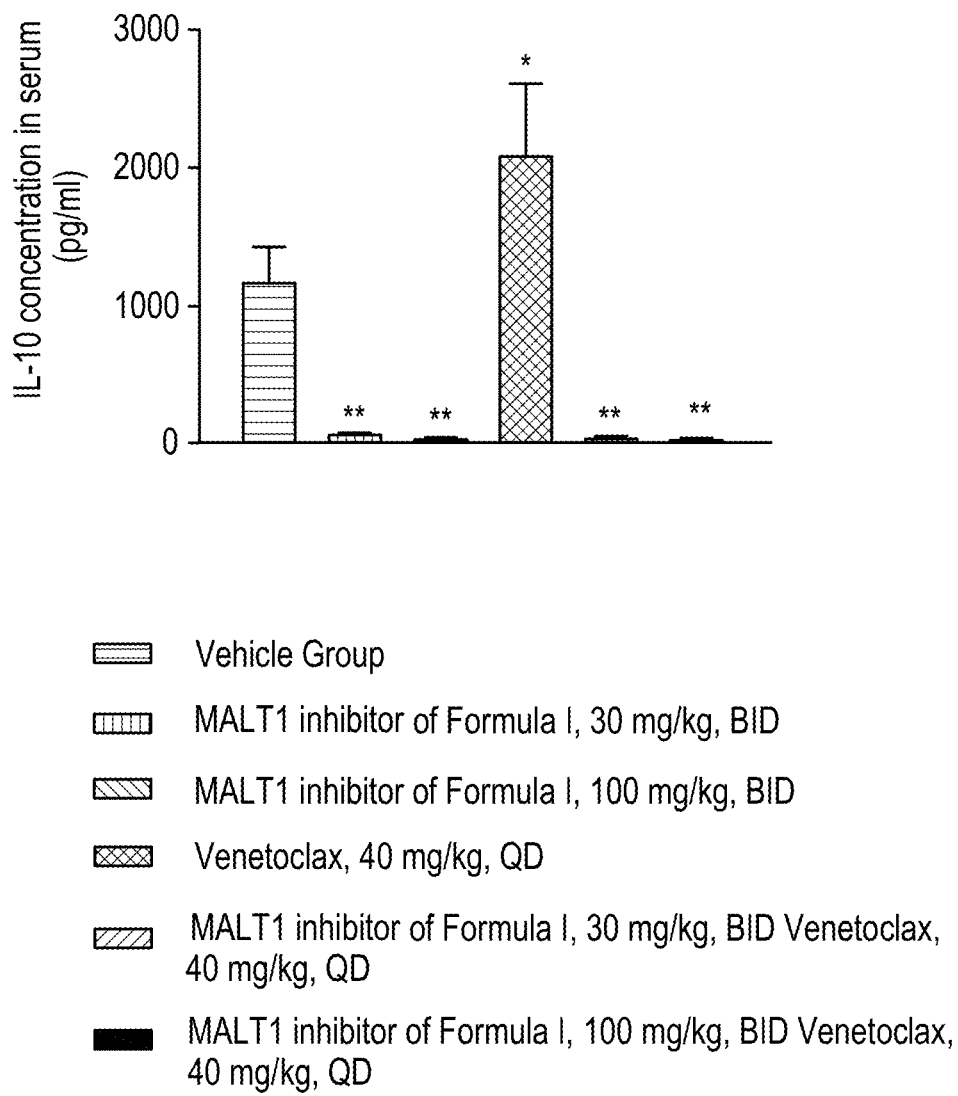
Figure 6E:
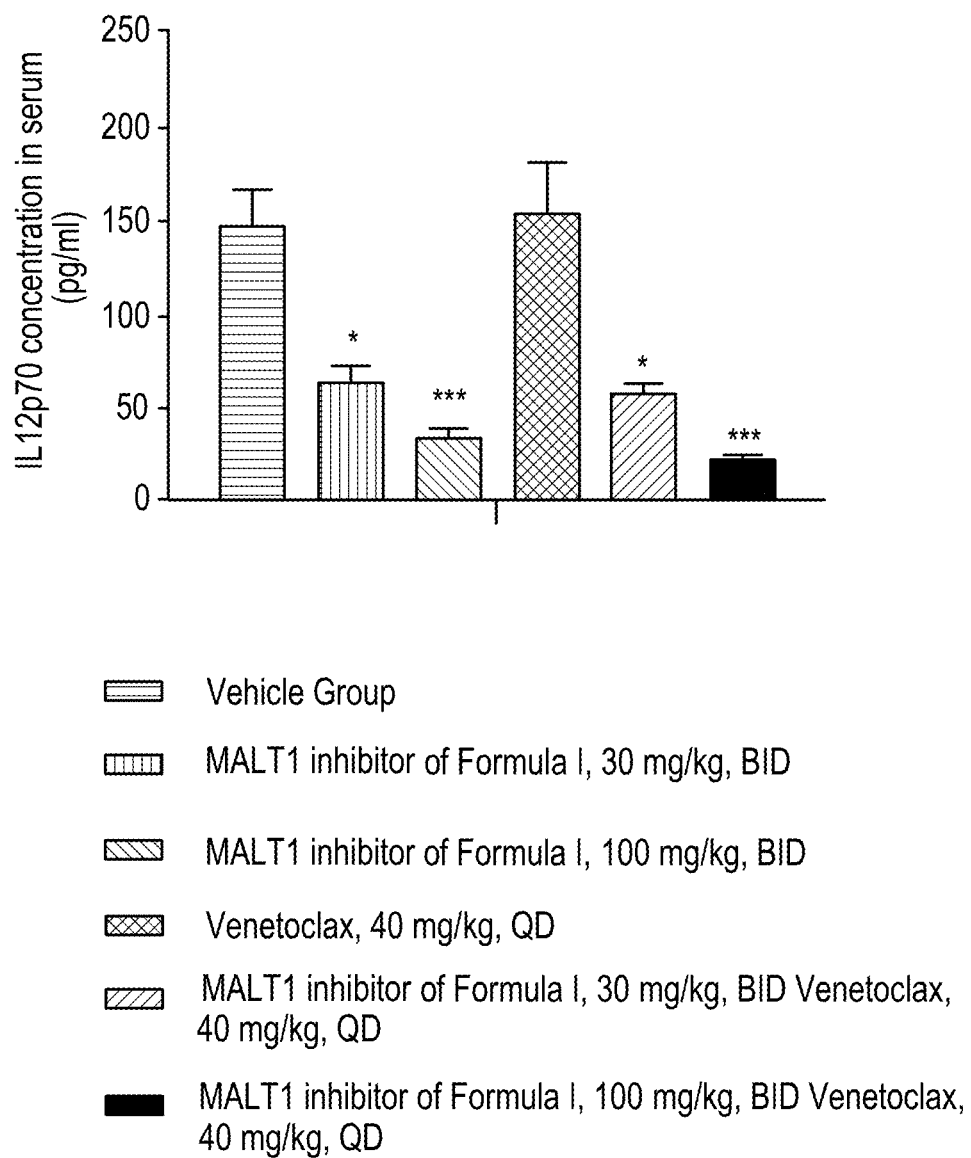

Monotherapy treatment with the MALT1 inhibitor of Formula I and combination therapy with the MALT1 inhibitor of Formula I and Venetoclax was able to decrease IL-10, TNF-α, and IL12p70 secretion levels in serum of OCI-LY3 tumor bearing mice (FIGS. 6C-6E). However, monotherapy with Venetoclax didn't show effect on cytokine secretion levels (FIGS. 6C-6F).

Discussion of Example 5

The MALT1 inhibitor of Formula I and Venetoclax are selective MALT1 and BCL2 inhibitors, respectively. In the OCI-LY3 model (CARD11 mut), monotherapy with the MALT1 inhibitor of Formula I treatment moderately inhibits in vivo growth of OCI-LY3 DLBCL CDX model while Venetoclax did not show any efficacy in this model. Unexpectedly, however, the combination therapy of the MALT1 inhibitor of Formula I and Venetoclax showed in vivo synergistic efficacy. Monotherapy treatment with the MALT1 inhibitor of Formula I or combination therapy with the MALT1 inhibitor of Formula I and Venetoclax were able to downregulate IL-10, TNF-α and IL12p70 secretion in serum of OCI-LY3 tumor bearing mice.

Taken together, the generated in vivo data support a combination of the MALT1 inhibitor of Formula I with Venetoclax in patients with B cell lymphomas.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a malignancy in a subject in need thereof, said method comprising:
administering to said subject a combination therapy comprising: (i) an inhibitor of mucosa-associated lymphoid tissue lymphoma translocation protein 1 (MALT1) having the structure of Formula (I)

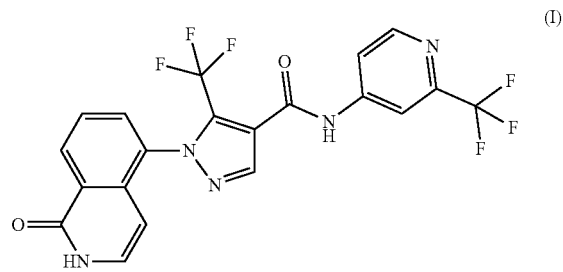

or a pharmaceutically acceptable salt, hydrate, polymorph, or solvates thereof, and (ii) an inhibitor of anti-apoptotic Bcl-2 family protein, wherein the combination therapy is administered to the subject in an amount effective to treat the malignancy in the subject.

2. The method of claim 1, wherein the malignancy is selected from the group consisting of a lymphoma, a leukemia, a carcinoma, and a sarcoma.

3. The method of claim 1, wherein the malignancy is a B-cell lymphoma.

4. The method of claim 3, wherein the B-cell lymphoma is selected from the group consisting of a diffuse large B-cell lymphoma (DLBCL), mantle cell lymphoma (MCL), follicular lymphoma (FL), transformed follicular lymphoma (tFL), marginal zone lymphoma (MZL), chronic lymphocytic leukemia (CLL), small lymphocytic lymphoma (SLL), Waldenström macroglobulinemia (WM), Burkitt lymphoma, hairy cell leukemia, primary central nervous system lymphoma, and primary intraocular lymphoma.

5. The method of claim 4, wherein the diffuse large B-cell lymphoma is activated B-cell (ABC)-DLBCL, germinal center B-cell (GCB)-DLBCL or non-GCB-DLBCL.

6. The method of claim 1, wherein the anti-apoptotic Bcl-2 family protein inhibitor is a BH3 protein mimetic.

7. The method of claim 1, wherein the anti-apoptotic Bcl-2 family inhibitor is selected from 4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide (navitoclax; ABT-263), 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199), N-(4-hydroxyphenyl)-3-[6-[(3S)-3-(morpholin-4-ylmethyl)-3,4-dihydro-1H-isoquinoline-2-carbonyl]-1,3-benzodioxol-5-yl]-N-phenyl-5,6,7,8-tetrahydroindolizine-1-carboxamide; hydrochloride (S55746, BLC201), (2R)-2-[5-[3-chloro-2-methyl-4-[2-(4-methylpiperazin-1-yl)ethoxy]phenyl]-6-(5-fluorofuran-2-yl)thieno[2,3-d]pyrimidin-4-yl]oxy-3-[2-[[2-(2,2,2-trifluoroethyl)pyrazol-3-yl]methoxy]phenyl]propanoic acid (S63845), (3'R,4S,6'R,7'S,8'E,11'S,12'R)-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.03,6.019,24]pentacosa-8,16(25),17,19(24)-tetraene]-15'-one (AMG-176), 17-chloro-5,13,14,22-tetramethyl-28-oxa-2,9-dithia-5,6,12,13,22-pentazaheptacyclo[27.7.1.1$^{4,7}$0.0$^{11,15}$0.0$^{16,21}$0.0$^{20,24}$0.0$^{30,35}$] octatriaconta-1(36),4(38),6,11,14,16,18,20,23,29(37),30,32,34-tridecaene-23-carboxylic acid (AZD-5991), 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide (ABT-737), 2-[(5E)-5-[(4-bromophenyl)methylidene]-4-oxo-2-sulfanylidene-1,3-thiazolidin-3-yl]-3-methylbutanoic acid (BH3I-1), 7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde (AT101; gossypol), 3-methyl-5-propan-2-yl-2-(1,6,7-trihydroxy-3-methyl-5-propan-2-ylnaphthalen-2-yl)naphthalene-1,6,7-triol (apogossypol), 3-[1-(1-adamantylmethyl)-5-methylpyrazol-4-yl]-6-[8-(1,3-benzothiazol-2-ylcarbamoyl)-3,4-dihydro-1H-isoquinolin-2-yl]pyridine-2-carboxylic acid (A-1331852), 2-[8-(1,3-benzothiazol-2-ylcarbamoyl)-3,4-dihydro-1H-isoquinolin-2-yl]-5-[3-[4-[3-(dimethylamino)prop-1-ynyl]-2-fluorophenoxy]propyl]-1,3-thiazole-4-carboxylic acid (A-1155463), N-[4-(2-tert-butylphenyl)sulfonylphenyl]-2,3,4-trihydroxy-5-[(2-propan-2-ylphenyl)methyl]benzamide (TW-37), 7-[5-[[4-[4-(dimethylsulfamoyl)piperazin-1-yl]phenoxy]methyl]-1,3-dimethylpyrazol-4-yl]-1-(2-morpholin-4-ylethyl)-3-(3-naphthalen-1-yloxypropyl)indole-2-carboxylic acid (A-12-10477), 2,3,5-trihydroxy-7-methyl-N-[(2R)-2-phenylpropyl]-6-[1,6,7-trihydroxy-3-methyl-5-[[(2R)-2-phenylpropyl]carbamoyl]naphthalen-2-yl]naphthalene-1-carboxamide (Sabutoclax; BI-97CI), (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[2-(hydroxymethyl)phenyl]pyrimidin-4-yl]methoxy]phenyl]propanoic acid (S64315; MIK665), (3'R,4S,6'R,7'R,8'E,11'S,12'R)-7'-[[(9aR)-1,3,4,6,7,8,9,9a-octahydropyrido[1,2-a]pyrazin-2-yl]methyl]-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.03,6.019,24]pentacosa-8,16(25),17,19(24)-tetraene]-15'-one (AMG397; murizatoclax), ethyl 2-amino-6-bromo-4-(1-cyano-2-ethoxy-2-oxoethyl)-4H-chromene-3-carboxylate (HA14-1), 2-[4-[(4-bromophenyl)sulfonylamino]-1-hydroxynaphthalen-2-yl]sulfanylacetic acid (UMI-77), [4,5-dichloro-1-[4,5-dichloro-2-(2-hydroxybenzoyl)-1H-pyrrol-3-yl]pyrrol-2-yl]-(2-hydroxyphenyl)methanone (Maritoclax; marinopyrrole A), (2Z)-2-[(5Z)-5-[(3,5-dimethyl-1H-pyrrol-2-yl)methylidene]-4-methoxypyrrol-2-ylidene]indole (Obatoclax; GX15-070), (4aR)-3-[(4'-Chloro[1,1'-biphenyl]-2-yl)methyl]-N-[[4-[[(1R)-3-(dimethylamino)-1-[(phenylthio)methyl]propyl]amino]-3-nitrophenyl]sulfonyl]-2,3,4,4a,5,6-hexahydro-1H-pyrazino[1,2-a]quinoline-8-carboxamide (S44563), [(2R,3S,6S,7R,8R)-3-[(3-formamido-2-hydroxybenzoyl)amino]-8-hexyl-2,6-dimethyl-4,9-dioxo-1,5-dioxonan-7-yl] 3-methylbutanoate (antimycin A), or derivatives thereof.

8. The method of claim 7, wherein the anti-apoptotic Bcl-2 family inhibitor is 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199).

9. The method of claim 1, wherein said MALT1 inhibitor of formula (I) and the anti-apoptotic Bcl-2 family protein inhibitor are administered concurrently or sequentially.

10. The method of claim 1, wherein said MALT1 inhibitor of formula (I) and the anti-apoptotic Bcl-2 family protein inhibitor are administered in a combined dosage form.

11. The method of claim 1, wherein said MALT1 inhibitor of formula (I) and the anti-apoptotic Bcl-2 family protein inhibitor are administered in separate dosage forms.

12. The method of claim 1, wherein the combination therapy comprises about 100 mg to about 400 mg of the MALT1 inhibitor of formula (I).

13. The method of claim 1, wherein the combination therapeutic comprises about 20 mg to about 400 mg of the anti-apoptotic Bcl-2 family protein inhibitor.

14. The method of claim 1, wherein the dose of the anti-apoptotic Bcl-2 family protein inhibitor is incrementally increased from about 20 mg/day to about 400/day with repeated administration of said combination therapy to avoid tumor lysis syndrome.

15. The method of claim 1, wherein the combination therapy is administered once a day.

16. The method of claim 1, wherein the combination therapy is administered twice a day.

17. The method of claim 1, wherein the MALT1 inhibitor of formula (I) is administered twice daily and the anti-apoptotic Bcl-2 family protein inhibitor is administered once daily.

18. The method of claim 1, where the MALT1 inhibitor of formula (I) is administered twice daily for at least 7 days, and once daily thereafter, and the anti-apoptotic Bcl-2 family protein inhibitor is administered once daily.

19. A method of reducing levels of regulatory T cells in a subject having a malignancy, said method comprising:
administering, to said subject having the malignancy, a combination therapy comprising: (i) an inhibitor of mucosa-associated lymphoid tissue lymphoma translocation protein 1 (MALT1) having the structure of Formula (I)

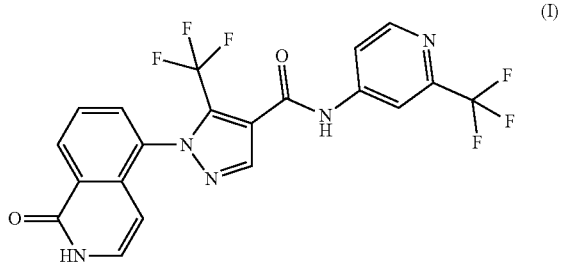

(I)

or a pharmaceutically acceptable salt, hydrate, polymorph, or solvates thereof, and (ii) an inhibitor of an anti-apoptotic Bcl-2 family protein, wherein the combination therapy is administered to the subject in an amount effective to reduce regulatory T cell levels in the subject relative to the levels of regulatory T cells in the subject prior to said administering.

20. The method of claim 19, wherein the malignancy is selected from the group consisting of a lymphoma, a leukemia, a carcinoma, and a sarcoma.

21. The method of claim 19, wherein the malignancy is a B-cell lymphoma.

22. The method of claim 21, wherein the B-cell lymphoma is selected from the group consisting of a diffuse large B-cell lymphoma (DLBCL), mantle cell lymphoma (MCL), follicular lymphoma (FL), transformed follicular lymphoma (tFL), marginal zone lymphoma (MZL), chronic lymphocytic leukemia (CLL), small lymphocytic lymphoma (SLL), Waldenström macroglobulinemia (WM), Burkitt lymphoma, hairy cell leukemia, primary central nervous system lymphoma, and primary intraocular lymphoma.

23. The method of claim 22, wherein the diffuse large B-cell lymphoma is activated B-cell (ABC)-DLBCL, germinal center B-cell (GCB)-DLBCL or non-GCB-DLBCL.

24. The method of claim 19, wherein the anti-apoptotic Bcl-2 family protein inhibitor is a BH3 protein mimetic.

25. The method of claim 19, wherein the anti-apoptotic Bcl-2 family inhibitor is selected from 4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide (navitoclax; ABT-263), 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (venetoclax; ABT-199), N-(4-hydroxyphenyl)-3-[6-[(3S)-3-(morpholin-4-ylmethyl)-3,4-dihydro-1H-isoquinoline-2-carbonyl]-1,3-benzodioxol-5-yl]-N-phenyl-5,6,7,8-tetrahydroindolizine-1-carboxamide; hydrochloride (S55746, BLC201), (2R)-2-[5-[3-chloro-2-methyl-4-[2-(4-methylpiperazin-1-yl)ethoxy]phenyl]-6-(5-fluorofuran-2-yl)thieno[2,3-d]pyrimidin-4-yl]oxy-3-[2-[[2-(2,2,2-trifluoroethyl)pyrazol-3-yl]methoxy]phenyl]propanoic acid (S63845), (3'R,4S,6'R,7'S,8'E,11''S, 12'R)-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.03,6.019,24]pentacosa-8,16 (25),17,19(24)-tetraene]-15'-one (AMG-176), 17-chloro-5, 13,14,22-tetramethyl-28-oxa-2,9-dithia-5,6,12,13,22-pentazaheptacyclo[27.7.1.1$^{4,7}$0.0$^{11,15}$0.0$^{16,21}$0.0$^{20,24}$0.0$^{30,35}$] octatriaconta-1(36),4(38),6,11,14,16,18,20,23,29(37),30,32, 34-tridecaene-23-carboxylic acid (AZD-5991), 4-[4-[[2-(4-chlorophenyl)methyl]piperazin-1-yl]-N-[[(2R)-4-(dimethylamino)-1-phenylsulfanylbutan-2-yl]amino]-3-nitrophenyl]sulfonylbenzamide (ABT-737), 2-[(5E)-5-[(4-bromophenyl)methylidene]-4-oxo-2-sulfanylidene-1,3-thiazolidin-3-yl]-3-methylbutanoic acid (BH3I-1), 7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde (AT101; gossypol), 3-methyl-5-propan-2-yl-2-(1,6,7-trihydroxy-3-methyl-5-propan-2-ylnaphthalen-2-yl)naphthalene-1,6,7-triol (apogossypol), 3-[1-(1-adamantylmethyl)-5-methylpyrazol-4-yl]-6-[8-(1,3-benzothiazol-2-ylcarbamoyl)-3,4-dihydro-1H-isoquinolin-2-yl]pyridine-2-carboxylic acid (A-1331852), 2-[8-(1,3-benzothiazol-2-ylcarbamoyl)-3,4-dihydro-1H-isoquinolin-2-yl]-5-[3-[4-[3-(dimethylamino)prop-1-ynyl]-2-fluorophenoxy] propyl]-1,3-thiazole-4-carboxylic acid (A-1155463), N-[4-(2-tert-butylphenyl)sulfonylphenyl]-2,3,4-trihydroxy-5-[(2-propan-2-ylphenyl)methyl]benzamide (TW-37), 7-[5-[[4-[4-(dimethylsulfamoyl)piperazin-1-yl]phenoxy]methyl]-1, 3-dimethylpyrazol-4-yl]-1-(2-morpholin-4-ylethyl)-3-(3-naphthalen-1-yloxypropyl)indole-2-carboxylic acid (A-12-10477), 2,3,5-trihydroxy-7-methyl-N-[(2R)-2-phenylpropyl]-6-[1,6,7-trihydroxy-3-methyl-5-[[(2R)-2-phenylpropyl]carbamoyl]naphthalen-2-yl]naphthalene-1-carboxamide (Sabutoclax; BI-97CI), (2R)-2-[5-[3-chloro-2-methyl-4-[2-(4-methylpiperazin-1-yl)ethoxy]phenyl]-6-(4-fluorophenyl) thieno[2,3-d]pyrimidin-4-yl]oxy-3-[2-[[2-[2-(hydroxymethyl)phenyl]pyrimidin-4-yl]methoxy]phenyl]propanoic acid (S64315; MIK665), (3'R,4S,6'R,7'R,8'E,11'S,12'R)-7'-[[(9aR)-1,3,4,6,7,8,9,9a-octahydropyrido[1,2-a]pyrazin-2-yl]methyl]-7-chloro-7'-methoxy-11',12'-dimethyl-13',13'-dioxospiro[2,3-dihydro-1H-naphthalene-4,22'-20-oxa-13 λ6-thia-1,14-diazatetracyclo[14.7.2.03,6.019,24]pentacosa-8,16(25),17,19(24)-tetraene]-15'-one (AMG397; murizatoclax), ethyl 2-amino-6-bromo-4-(1-cyano-2-ethoxy-2-oxoethyl)-4H-chromene-3-carboxylate (HA14-1), 2-[4-[(4-bromophenyl)sulfonylamino]-1-hydroxynaphthalen-2-yl] sulfanylacetic acid (UMI-77), [4,5-dichloro-1-[4,5-dichloro-2-(2-hydroxybenzoyl)-1H-pyrrol-3-yl]pyrrol-2-yl]-(2-hydroxyphenyl)methanone (Maritoclax; marinopyrrole A), (2Z)-2-[(5Z)-5-[(3,5-dimethyl-1H-pyrrol-2-yl)methylidene]-4-methoxypyrrol-2-ylidene]indole (Obatoclax; GX15-070), (4aR)-3-[(4'-Chloro[1,1'-biphenyl]-2-yl)methyl]-N-[[4-[[(1R)-3-(dimethylamino)-1-[(phenylthio)methyl]propyl]amino]-3-nitrophenyl]sulfonyl]-2,3,4,4a,5,6-hexahydro-1H-pyrazino[1,2-a]quinoline-8-carboxamide (S44-563), [(2R,3S,6S,7R,8R)-3-[(3-formamido-2-hydroxybenzoyl)amino]-8-hexyl-2,6-dimethyl-4,9-dioxo-1,5-dioxonan-7-yl] 3-methylbutanoate (antimycin A), or derivatives thereof.

26. The method of claim 25, wherein the anti-apoptotic Bcl-2 family inhibitor is 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2, 3-b]pyridin-5-yloxy)benzamide (venetoclax; ABT-199).

27. The method of claim 19, wherein the combination therapy comprises about 100 mg to about 400 mg of the MALT1 inhibitor of formula (I).

28. The method of claim 19, wherein the combination therapeutic comprises about 20 mg to about 400 mg of the anti-apoptotic Bcl-2 family protein inhibitor.

29. The method of claim 19, wherein the dose of the anti-apoptotic Bcl-2 family protein inhibitor is incrementally increased from about 20 mg/day to about 400/day with repeated administration of said combination therapy to avoid tumor lysis syndrome.

30. The method of claim 19, wherein the combination therapy is administered once a day.

31. The method of claim 19, wherein the combination therapy is administered twice a day.

32. The method of claim 19, where the MALT1 inhibitor of formula (I) is administered twice daily for at least 7 days, and once daily thereafter, and the anti-apoptotic Bcl-2 family protein inhibitor is administered once daily.

* * * * *